United States Patent [19]

Meyer et al.

[11] 4,444,770

[45] Apr. 24, 1984

[54] NEW IMIDAZOAZOLE-ALKENOIC ACID AMIDE COMPOUNDS, INTERMEDIATE PRODUCTS FOR THEIR PRODUCTION, THEIR PRODUCTION, AND THEIR MEDICINAL USE

[75] Inventors: Horst Meyer; Harald Horstmann; Eike Möller, all of Wuppertal; Bernward Garthoff, Hilden, all of Fed. Rep. of Germany

[73] Assignee: Bayer Aktiengesellschaft, Leverkusen, Fed. Rep. of Germany

[21] Appl. No.: 263,400

[22] Filed: May 13, 1981

[30] Foreign Application Priority Data

May 29, 1980 [DE] Fed. Rep. of Germany ....... 3020421
Nov. 15, 1980 [DE] Fed. Rep. of Germany ....... 3043158

[51] Int. Cl.$^3$ .................. C07D 513/04; C07D 277/60

[52] U.S. Cl. ................................ 424/248.5; 546/167; 546/199; 424/248.53; 546/271; 548/154; 424/248.54; 548/218; 548/126; 424/248.55; 548/262; 548/324; 424/248.56; 548/318; 548/323; 424/248.57; 424/248.58; 424/250; 424/258; 424/263; 424/267; 424/269; 424/270; 424/272; 424/273 R; 544/80; 544/81; 544/134; 544/137; 544/138; 544/139; 544/133; 544/323; 544/333; 544/336; 544/405; 546/1

[58] Field of Search ........... 424/248.5, 248.53, 248.54, 424/248.55, 248.56, 248.57, 248.58, 250, 258, 263, 267, 269, 270; 542/421, 422, 435, 436, 437, 439; 544/80, 81, 134, 137, 138, 139, 133, 323, 333, 336, 405; 546/1, 167, 199, 271; 548/154, 218, 126, 262, 324, 318, 323

[56] References Cited

U.S. PATENT DOCUMENTS

| | | | |
|---|---|---|---|
| 3,804,823 | 4/1974 | Fisher et al. | 548/126 |
| 3,957,977 | 5/1976 | Hoffmann et al. | 548/154 |
| 4,042,583 | 8/1977 | Acheson | 548/324 |
| 4,263,311 | 4/1981 | Bender | 548/154 |
| 4,265,898 | 5/1981 | Horstmann et al. | 548/126 |
| 4,276,415 | 6/1981 | Degen et al. | 548/324 |

OTHER PUBLICATIONS

Barnish et al., J. Med. Chem. 1980 23, 117-121.

*Primary Examiner*—Arthur P. Demers
*Attorney, Agent, or Firm*—Sprung, Horn, Kramer & Woods

[57] ABSTRACT

The invention relates to imidazoazole-alkenoic acid amides of Formula (I) and methods for their production. Also included in the invention are compositions containing said alkenoic acid amides and methods for the use of said alkenoic acid amides and the compositions containing them. In addition, the invention includes the intermediate carbonyl compounds of Formula (II) and the intermediate alkenoic acids of Formula (V) as well as methods for their preparation.

15 Claims, No Drawings

NEW IMIDAZOAZOLE-ALKENOIC ACID AMIDE COMPOUNDS, INTERMEDIATE PRODUCTS FOR THEIR PRODUCTION, THEIR PRODUCTION, AND THEIR MEDICINAL USE

The present invention relates to certain new imidazoazole-alkenoic acid amide compounds, to several processes for their production, to their use as antihyper-tensive agents, diuretic agents and uricosuric agents, and to new intermediate products which are used in their production.

It has already been disclosed that certain imidazothiadiazoles have biological actions, in particular antithrombotic and antimicrobial properties (see DE-OS (German Published Specification) No. 2,823,682).

It is also known that certain imidazothiadiazoles and imidazothiazole-sulphonamides have cerebral actions (see J. med. Chem. 1980, 117, I. C. Barnisch et al.).

According to the present invention there are provided compounds which are imidazoazole-alkenoic acid amides of the general formula

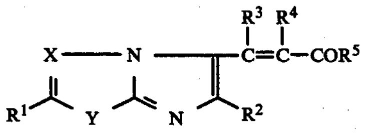

(I)

or a salt thereof, in which

X represents N or CH,

Y represents S, O, NH or N-alkyl, $R^1$ and $R^2$ are identical or different and each represent a hydrogen atom or a straight-chain, branched or cyclic alkyl, alkenyl or alkinyl radical, optionally substituted by phenyl, cyano, hydroxyl or halogen, the carbon chain of the alkyl radical optionally being interrupted by O, S, NH, N-alkyl, or N-aralkyl;

represent a phenyl, naphthyl, furyl, thienyl, pyrimidyl, pyrazinyl, quinolyl, isoquinolyl or pyridyl radical which is optionally substituted by 1, 2 or 3 identical or different substituents selected from alkyl, alkoxy, halogen nitro, trifluoromethyl and $SO_n$-alkyl (in which n is 0, 1 or 2); represent a $SO_n$-alkyl group (in which n is 0, 1 or 2):

represent a radical of the formula

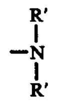

(wherein R′ and R″ are identical or different and each represent a hydrogen atom or an aralkyl, aryl or alkyl radical, it being possible for the alkyl radicals in turn to be interrupted by O, S, NH or N-alkyl, or in which R′ and R″, together with the nitrogen atom, form a 5-membered to 7-membered ring, which in turn optionally contains 1 or 2 further hetero-atoms selected from the group consisting of O, S and NH, in which the nitrogen atom can be substituted by alkyl, aryl or aralkyl);

or represent a radical of the general formula COR‴ (wherein R‴ denotes a hydrogen atom or a hydroxyl, alkyl, alkoxy, alkenyl, alkenoxy, alkinyl, aralkoxy or aryloxy radical or a radical of the formula

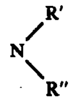

wherein R′ and R″ have the meanings given above), $R^3$ represents a hydrogen atom or a trifluoromethyl or alkyl radical, $R^4$ represents a hydrogen atom, a cyano group, a halogen atom or a nitro or $SO_n$-alkyl radical (in which n is 0, 1 or 2), or $R^4$ represents an alkoxy radical or a straight-chain, branched or cyclic alkyl, alkenyl or alkinyl radical, the carbon chain of the alkyl radical optionally being substituted by halogen or cyano and optionally being interrupted by O, S, NH, N-alkyl, N-aryl or N-aralkyl, or a radical of the formula COR‴ (wherein R‴ has the meaning given above in the definition of $R^1$ and $R^2$ and is identical to or different from these radicals) and $R^5$ represents an amino group of the formula

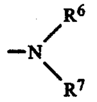

in which (a) $R^6$ denotes a hydrogen atom, an aryl radical or a straight-chain, branched or cyclic, saturated or unsaturated aliphatic hydrocarbon radical which is optionally interrupted by O, S, N, N-alkyl, NH, N-aryl or N-aralkyl and which is optionally substituted by hydroxyl, alkoxy, alkyl, trifluoromethyl, halogen, phenyl, alkoxycarbonyl or dialkylamino, the two alkyl radicals optionally forming, together with the N atom, a 5-membered to 7-membered ring which is optionally interrupted by a hetero-atom selected from O, S, NH and N-alkyl, and these abovementioned alkyl and phenyl radicals in turn optionally being substituted by halogen, trifluoromethyl, alkyl, aryl, aralkyl, alkoxy, alkylmercapto or $SO_2$-alkyl or (b) $R^6$, together with $R^7$ and with the nitrogen atom, forms a 3-membered to 8-membered saturated or unsaturated ring which optionally contains 1 or 2 further hetero-atoms selected from oxygen, sulphur and nitrogen, the nitrogen optionally being substituted by hydrogen, alkyl, aryl or aralkyl, and it being possible for this 3-membered to 8-membered ring to be substituted by 1, 2, 3 or 4 identical or different substituents selected from alkyl, halogen, aryl, aralkyl, alkoxycarbonyl, hydroxyalkyl, alkoxyalkyl and trifluoromethyl, or it being possible for this ring to be fused onto an optionally substituted aromatic ring, and (c) $R^7$ has the meaning of $R^6$ given under (a), it being possible for $R^7$ and $R^6$ to be identical or different, or (d) one of the two radicals $R^6$ or $R^7$ represents a group of the general formula

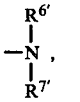

the radicals $R^{6'}$ and $R^{7'}$ having the meaning of $R^6$ and $R^7$ given under (a) and (b) (hydrazines), and their stereoisomeric forms in the form of enantiomers, diastereomers and Z/E-isomers.

As used herein and unless otherwise specified, the terms "alkyl" "alkoxy or alkylmercapto" preferably contain 1 to 8 (particularly 1 to 4) carbon atoms; the term "cycloalkyl" preferably contains 4 to 7, especially 5 to 6 ring members; the terms "alkayl" and "alkinyl" preferably contain up to 8 (especially up to 4) carbon atoms; the term "halogen" preferably refers to chlorine, fluorine or bromine, expecially chlorine or fluorine; the terms "aralkyl" and "aralkoxy" preferably refers to groups which are mono- or bi-cyclic carbocylic aryl in the aromatic position with 1 to 4 (especially 1 to 2) carbon atoms in the alkyl position; the terms "aryl" and "aryloxy" preferably refer to groups in which the aryl portion is mono- or bi-cyclic carbocyclic aryls; the term "alkenoxy" preferably contains up to 8 (especially up to 4) carbon atoms; the term "alkoxycarbonyl" refers to groups preferably containing 1 to 8, (especially 1 to 4) carbon atoms in the alkoxy position; the term "dialkylamino" preferably contains 1 to 8 (especially 1 to 4 or 1 to 2 carbon atoms in each alkyl group; and the terms "hydroxyalkyl" and "alkoxyalkyl" preferably contain 1 to 8 (especially 1 to 4) carbon atoms in each alkyl moiety.

According to the present invention there is further provided a process for the production of compounds as above-mentioned according to the present invention in which (a) a carbonyl compound of the formula

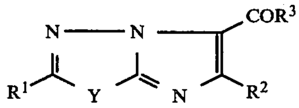 (II)

in which

X, Y, $R^1$, $R^2$ and $R^3$ have the abovementioned meaning, is reacted with a phosphonate compound of the formula

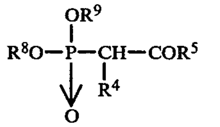 (III)

in which $R^4$ and $R^5$ have the abovementioned meaning and $R^8$ and $R^9$ independently represent an optionally substituted alkyl or aralkyl radical, in the presence of a strong base and an inert organic solvent, at a temperature between −20° C. and +40° C., or (b) a carbonyl compound of the formula (II), as defined above, is reacted with an acetamide derivative of the formula $R^4—CH_2—COR^5$ (IV)

in which $R^4$ and $R^5$ have the abovementioned meaning, in the presence of an acid or basic catalyst and optionally in the presence of an inert organic solvent, at a temperature between 20° and 200° C., or (c) an alkenoic acid of the formula

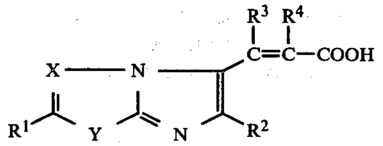 (V)

in which

X, Y, $R^1$, $R^2$, $R^3$ and $R^4$ have the abovementioned meaning, is amidated, optionally after activating the carboxyl group via the corresponding acid halide, with an amine of the formula

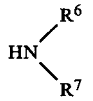 (VI)

in which $R^6$ and $R^7$ have the abovementioned meaning, optionally in the presence of an inert organic solvent at a temperature between 20° and 150° C.

The compounds according to the invention can exist in stereoisomeric forms, depending on the choice of starting substances, and these stereoisomeric forms either behave as mirror images (enantiomers) or do not behave as mirror images (diastereomers). The present invention relates to both the antipodes and the racemic forms as well as the diastereomer mixtures. The racemic forms can be separated into the stereoisomerically uniform constituents in a known manner, as can the diastereomers (see, for example, E. L. Eliel, Stereochemistry of Carbon Compounds, McGraw Hill, 1962).

Moreover, this application also encompasses the possible Z/E-isomers which result from the double bond in the side chain and can be prepared by known processes or converted into one another by known processes.

The carbonyl compounds of the formula (II) which can be employed as starting compounds are novel, but they can be prepared by methods analogous to the following known methods:

Method (i)

L. Pentimalli et al., Boll.Sci.Fac.Chim.Ind. Bologna 23, 181 (1965); see Chem. Abstr. 63, 17848 e (1965).

Method (ii)

D. Bower et al.; J.Chem.Soc. 1955, 2834.

Method (iii)

A. Hetzheim et al., Chem.Ber. 103, 3533 (1970).

Method (iv)

H. Beyer et al., Z. Chem. 2, 152 (1962).

Method (v)

S. Kano, Yakugku Zasski 92, 935 (1972).

The present invention thus also relates to new compounds of the formula (II)

in which

X, Y, $R^1$, $R^2$ and $R^3$ have the meanings which have been given for these substituents in the definition of compounds of the formula (I).

The alkenoic acids of the formula (V) which can be employed as starting compounds are also novel. They can be prepared by known methods, by a process in which (α) a carbonyl compound of the formula

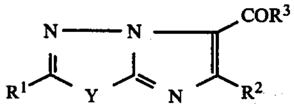

(II)

in which

X, Y, $R^1$, $R^2$ and $R^3$ have the abovementioned meaning is reacted with a phosphonate compound of the formula

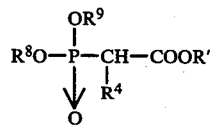

(VII)

in which $R^4$, $R^8$ and $R^9$ have the abovementioned meaning and

R' represents an optionally substituted alkyl or aralkyl radical, to give an alkenoic acid ester, which is then saponified in the presence of a base to give the corresponding alkenoic acid of the general formula (V) (compare W. S. Wadsworth et al., JACS 83, 1733 (1961)) or (β) if a compound of formula (V) is required in which $R^3$ denotes a hydrogen atom, an aldehyde of the formula

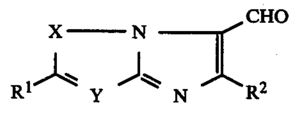

(VIII)

in which

X, Y, $R^1$ and $R^2$ have the abovementioned meaning, is subjected to a condensation reaction with a malonic acid of the formula

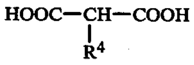

(IX)

in which $R^4$ has the above mentioned meaning, in the presence of an inert solvent and optionally in the presence of a condensing agent (compare G. Jones, Org. Reactions, Volume 15, page 204 et seq.).

The phosphonate compounds of the formula (III) employed in carrying out the preparation process according to the invention are known, or they can be prepared by known methods (see I. Shahak et al. Isr. J. Chem. 7, 585 (1969)).

Examples which may be mentioned of strong bases to be used in carrying out process variant (a) are: alkali metal hydrides (such as sodium hydride, potassium hydride and lithium hydride), alkali metal alcoholates (such as sodium ethylate, potassium ethylate or potassium methylate) or alkali metal-alkyls (such as methyl-lithium or butyl-lithium).

The acetamide derivatives of the formula (IV) employed in carrying out process variant (b) are known, or they can be prepared by known methods (see (a) British Patent No. 715,896 (1954); and C.A. 49, 13290d 1955); and see (b) German Patent No. 1,142,859 (1960); and C.A. 59, 7377c (1963)).

Acid or basic catalysts are preferably employed in this process variant (b), and the following may be mentioned as examples: basic amines (such as dialkylamines, piperidine or pyridine), inorganic acids (in particular hydrochloric acid) or condensing agents (such as carboxylic acid anhydrides).

The alkenoic acids of the formula (V) employed according to process variant (c) have not yet been disclosed, but they can be prepared in a manner which is in itself known by the abovementioned processes. The activation of the free carboxyl group appropriate for the reaction with amines of the formula (VI) is preferably effected via the corresponding acid halide, in particular via the corresponding acid chloride, using agents which form halides (such as thionyl chloride, phosphorus trichloride and phosphorus pentachloride).

The customary inert organic solvents can be employed as diluents in all the processes according to the invention. These solvents include, preferably, ethers (such as diethyl ether), glycol ethers (such as glycol dimethyl ether, dioxane or tetrahydrofuran), alcohols (such as methanol, ethanol, propanol, butanol or benzyl alcohol), sulphoxides (such as dimethylsulphoxide), bases (such as pyridine, quinoline or picoline), hydrocarbons (such as benzene, toluene or xylene), and dimethylformamide.

In the preparation of the alkenoic acids of the formula (V), the bases which are preferably used for saponification of the corresponding esters are: alkali metal hydroxides (such as sodium hydroxide or potassium hydroxide), and alkaline earth metal hydroxides, (such as barium hydroxide or calcium hydroxide).

Condensing agents which are preferably used in the preparation via the aldehydes of the formula (VIII) and malonic acids of the formula (IX) are: pyridine, substituted pyridine derivatives (such as dialkylaminopyridines), quinoline, isoquinoline, dialkylamines (such as dimethylamine and dibutylamine), pyrrolidine, piperidine and similar nitrogen-containing organic bases.

Preferred compounds according to the invention are those in which

X represents N or CH,

Y represents S, O, NH or N-alkyl with 1 to 4 carbon atoms, $R^1$ and $R^2$ are identical or different and each represent a hydrogen atom or a straight-chain, branched or cyclic alkyl, alkenyl or alkinyl radical which has up to 6 carbon atoms and is optionally substituted by phenyl, cyano, hydroxyl, fluorine, chlorine or bromine, the carbon chain of the alkyl radical optionally being interrupted by O, S, NH, N-alkyl with 1 to 4 carbon atoms or N-benzyl;

represent a phenyl, naphthyl, furyl, thienyl, pyrimidyl, pyrazinyl, quinolyl, isoquinolyl or pyridyl radical which is optionally substituted by 1, 2 or 3 identical or different substituents selected from nitro, trifluoromethyl, fluorine, chlorine, bromine, alkyl, alkoxy and $SO_n$-alkyl (in which n is 0, 1 or 2), the alkyl and alkoxy radicals mentioned each containing 1 to 4 carbon atoms;

represent a $SO_n$- $C_1$ to $C_4$ alkyl group (in which n is 0, 1 or 2);

represent a radical of the general formula

(wherein R' and R'' are identical or different and each represent a hydrogen atom, a benzyl or phenyl radical or an alkyl radical with 1 to 6 carbon atoms, it being possible for the alkyl radicals in turn to be interrupted by O, S or N— $C_1$ to $C_4$ alkyl, or in which R' and R'', together with the nitrogen atom, form a 5-membered to 7-membered ring, which can in turn contain 1 or 2 identical or different hetero-atoms selected from oxygen, sulphur and nitrogen, the nitrogen optionally being substituted by hydrogen, alkyl with 1 to 4 carbon atoms, phenyl or benzyl);

or represent a radical of the formula COR''', (wherein R''' denotes a hydrogen atom, a hydroxyl, alkyl or alkoxy radical with in each case 1 to 6 carbon atoms, a phenoxy or benzyloxy radical, an alkenoxy radical with up to 4 carbon atoms or a radical of the formula

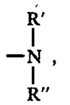

(wherein R' and R'' have the immediately above-mentioned meaning)), $R^3$ represents a hydrogen atoma, a trifluoromethyl radical or an alkyl radical with 1 to 4 carbon atoms, $R^4$ represents a hydrogen atom, a cyano or nitro radical, a fluorine, chlorine or bromine atom or a $SO_n$—$C_1$ to $C_4$ alkyl radical in which n is 0, 1 or 2), or an alkoxy radical with 1 to 4 carbon atoms or a straight-chain, branched or cyclic alkyl, alkenyl or alkinyl radical with in each case up to 6 carbon atoms, the alkyl radical optionally being substituted by fluorine, chlorine, bromine or cyano and optionally being interrupted by O, S, NH, N-benzyl or N—$C_1$ to $C_4$ alkyl, or a radical of the general formula COR''', (wherein R''' has the meaning given above in the definition of $R^1$ and $R^2$, and can be identical to or different from these substituents), and $R^5$ represents an amino group of the formula

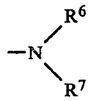

in which (a) $R^6$ denotes a hydrogen atom, a phenyl radical or a straight-chain, branched or cyclic, saturated or unsaturated aliphatic hydrocarbon radical which has up to 10 carbon atoms and is optionally interrupted by O, S, N, N—$C_1$ to $C_4$ alkyl, NH, N-phenyl or N-benzyl and is optionally substituted by hydroxyl, alkoxy, alkyl, fluorine, chlorine, bromine, phenyl, alkoxycarbonyl or dialkylamino with in each case 1 to 4 carbon atoms in the alkyl and alkoxy radicals, the two alkyl radicals, with the N atoms, optionally forming a 5-membered to 7-membered ring which is optionally interrupted by O, S, NH or N—$C_1$ to $C_4$ alkyl, and the abovementioned alkyl and phenyl radicals in turn optionally being substituted by fluorine, chlorine, bromine, trifluoromethyl, phenyl, benzyl, alkyl, alkoxy or $SO_2$-alkyl, with in each case 1 to 4 carbon atoms in the alkyl and alkoxy radicals, or (b) $R^6$ together with $R^7$ and with the nitrogen atom, forms a 4-membered to 7-membered ring which optionally contains 1 or 2 further hetero-atoms selected from oxygen, sulphur and nitrogen, the nitrogen optionally being substituted by hydrogen, $C_1$ to $C_4$ alkyl, phenyl or benzyl, and it being possible for this 4-membered to 7-membered ring to be substituted by 1 to 4 identical or different substituents selected from halogen, trifluoromethyl, phenyl, benzyl, alkyl, hydroxyalkyl, alkoxyalkyl and alkoxycarbonyl with in each case 1 to 4 carbon atoms in the alkyl and alkoxy radicals, or it being possible for this ring to be fused onto an aromatic ring (preferably a monocyclic carbocyclic aromatic ring) which is optionally substituted by fluorine, chlorine, bromine, nitro or hydroxyl, and (c) $R^7$ has the meaning of $R^6$ given immediately above under (a) it being possible for $R^7$ and $R^6$ to be identical or different, or (d) one of the two radicals $R^6$ or $R^7$ represents a group of the formula

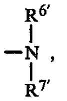

wherein the radicals $R^{6'}$ and $R^{7'}$ have the meaning of $R^6$ and $R^7$ given immediately above under (a) and (b) (hydrazines).

Particularly preferred compounds according to the invention are those in which

X represents N or CH,

Y represents S, O or NH $R^1$ and $R^2$ are identical or different and each represent a hydrogen atom, a trifluoromethyl or phenyl radical, an alkyl or alkenyl radical which has up to 6 carbon atoms and is optionally substituted by fluorine, chlorine, hydroxyl, trifluoromethyl or alkyl or alkoxy with in each case 1 or 2 carbon atoms;

represent a pyridyl, thienyl, furyl, naphthyl, pyrimidyl, pyrazinyl, quinolyl or isoquinolyl radical;

represent a radical of the formula

(wherein R' and R'' are identical or different and each represent a hydrogen atom, a benzyl or phenyl radical or a straight-chain, branched or cyclic alkyl radical with up to 6 carbon atoms, it being possible for the alkyl radicals in turn to be interrupted by O, S or N-$C_1$ or $C_2$ alkyl or wherein R' and R'', together with the nitrogen atom, form a 5-membered to 7-membered ring, which can in turn contain 1 or 2 identical or different hetero-atoms selected from oxygen, sulphur and nitrogen, the nitrogen optionally being substituted by hydrogen, alkyl with 1 or 2 carbon atoms, phenyl or benzyl); or represent a radical of the formula COR''', (wherein R''' denotes a hydrogen atom, a hydroxyl radical, an alkyl or alkoxy radical with in each case up to 4 carbon atoms, a phenoxy or benzyloxy radical or a radical of the formula

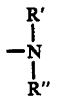

wherein R' and R'' have the abovementioned meaning) $R^3$ represents a hydrogen atom, a trifluoromethyl radical or an alkyl radical with 1 to 4 carbon atoms, $R^4$ represents a hydrogen atom, an alkyl or alkoxy radical which has in each case 1 to 4 carbon atoms and is optionally interrupted by oxygen and optionally substituted by fluorine, chlorine or cyano, or a cyano or nitro radical or a radical of the formula COR''', (wherein R''' has the meaning given immediately above in the definition of $R^1$ and $R^2$), or $R^4$ represents $SO_n$-$C_1$ to $C_4$ alkyl (in which n is 0 or 2), and $R^5$ represents an amino group of the formula

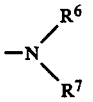

in which (a) $R^6$ denotes a hydrogen atom, a phenyl radical or a straight-chain, branched, cyclic, saturated or unsaturated hydrocarbon radical which has up to 10 carbon atoms, is optionally interrupted by O, S, N, NH, N-phenyl or N-benzyl and is optionally substituted by hydroxyl, alkoxy, fluorine, chlorine, bromine, phenyl, alkoxycarbonyl or dialkylamino with in each case 1 to 4 carbon atoms in the alkyl and alkoxy radicals, the two alkyl radicals optionally forming, with the N atom, a 5-membered or 6-membered ring which is optionally interrupted by O, S or NH, and the abovementioned alkyl and phenyl radicals in turn being optionally substituted by fluorine, chlorine, bromine, trifluoromethyl, alkyl, alkoxy or $SO_2$-alkyl with in each case 1 to 4 carbon atoms in the alkyl and alkoxy radicals, or (b) $R^6$, together with $R^7$ and with the nitrogen atom, forms a 4-membered to 7-membered ring which optionally contains 1 or 2 further heteroatoms selected from oxygen, sulphur and nitrogen, the nitrogen optionally being substituted by hydrogen, $C_1$ or $C_2$ alkyl, phenyl or benzyl, and it being possible for this 4-membered to 7-membered ring to be substituted by 1 to 4 identical or different substitutents selected from fluorine, chlorine, trifluoromethyl, alkyl, hydroxyalkyl, alkoxyalkyl and alkoxycarbonyl with in each case 1 to 4 carbon atoms in the alkyl and alkoxy radicals, or it being possible for this ring to be fused onto an aromatic ring is optionally substituted by fluorine, chlorine, nitro or hydroxyl, and (c) $R^7$ has the meaning of $R^6$ given immediately above under (a), it being possible for $R^7$ and $R^6$ to be identical or different, or (d) one of the two radicals $R^6$ or $R^7$ represents a group of the general formula

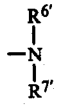

wherein the radicals $R^{6'}$ and $R^{7'}$ have the meaning of $R^6$ and $R^7$ given immediately above under (a) and (b) (hydrazines).

Surprisingly, the new compounds according to the invention are distinguished by powerful biological actions. In particular, they have pronounced diuretic and saluretic actions and can therefore be used as diuretic agents, saluretic agents and antihypertensive agents. In animal experiments on mice, rats and dogs, it is found that the compounds according to the invention even have a pronounced diuretic and saluretic action, coupled with a good tolerance, when administered orally in dosages of less than 10 mg/kg. With knowledge of the state of the art, these advantageous properties could not be expected.

The surprising and advantageous actions of the compounds according to the invention can be determined by the following test methods:

(A) Antihypertensive action on rats

The effect on blood pressure is determined on rats suffering from Goldblatt's hypertension, in accordance with the method of H. Breuninger: Methode zur unblutigen Messung des Blutdruckes an Kleintieren, (Non-surgical method for measuring the blood pressure of small animals), Arzneimittelforsch. 6, 222–225 (1965).

(B) Diuretic action in rats

Fasting male rats weighing 150 to 250 g (SPF, Wistar, in each case n=4 pairs) are treated perorally with 10 ml/kg of tylose suspension (0.5% strength), as controls, or perorally with 100 mg/kg of test substance in 10 ml/kg, perorally, of tylose suspension by means of a stomach tube. The animals are put into metabolism cages and the excretion of urine and elimination of electrolytes are determined over a period of 6 hours ($Na^+$ and $K^+$ determination: IL-flame photometer).

(C) Diuretic action in dogs

A catheter is passed into the bladder of fasting, wake female beagles and the excretion of urine and elimination of electrolytes are determined over a period of 180 minutes (fractions collected over periods of in each case 30 minutes).

During this period, the animals receive an electrolyte solution intravenously by continuous infusion, and the test substance is administered orally in 1 ml/kg of tylose suspension (0.5% strength) at the start of the experiment.

The $Na^+$, $K^+$, chlorine and bicarbonate content and pH value of the urine are analysed.

(D) Diuretic action in mice

Fasting male SPF mice weighing 20 to 25 g (n=6×3 animals/cage) receive 100 ml/kg of tylose suspension (0.5% strength), as controls, or 100 mg/kg of test substance in tylose suspension orally. The excretion of urine and the elimination of $Na^+$ and $K^+$ and uric acid are determined in metabolism cages over periods of 2 and 4 hours.

(E) Phenol red retention test in rats

The effect of compounds according to the invention on the level of phenol red in the blood is determined on fasting male rats (SPF-Wistar, weight: 180 to 250 g), in order to detect uricosuric activity. Following the method of E. Kreppel (Med. exp. 1 (1959), 285–289), 75 mg/kg of phenol red in 5 ml/kg of sodium chloride solution is administered intraperitoneally to each of 8 animals, after they have been given either 10 mg/kg of tylose suspension (0.5% strength), as controls, or 100 mg/kg of test substance in tylose suspension 30 minutes beforehand. Plasma is obtained, by puncture of the retroorbital venus plexus, 30, 60 and 120 minutes after administration of phenol red, or 60, 90 and 150 minutes after administration of the substance, and NaOH is added to the plasma and the extinction is measured at 546 nm in a photometer (Eppendorf).

A potential uricosuric activity exists if the extinction values are significantly greater than those in the control group.

The new compounds according to the invention are substances which can be used as medicaments. When administered orally or parenterally, they cause an increase in the elimination of water and salts and can thus be used for the treatment of oedematous and hypertonic conditionsand for eliminating toxic substances.

Moreover, the compounds can be used in cases of acute renal insufficiency. In particular, they also exhibit an advantageous uricosuric action.

As stated above, the invention also relates to the use in medicine of the compounds of the invention.

The present invention provides pharmaceutical compositions containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides medicaments in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of suspensions, solutions and emulsions of the active ingredient in aqueous or non-aqueous diluents, or syrups.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up on microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

for parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of these mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills dragees, capsules, suppositories and ampoules. Some of these forms may be made up for delayed release of the active ingredient. Some, such as capsules, include a protective envelope which renders the portions of the medicament physically discrete and coherent.

The preferred daily dose for parenteral administration of the medicaments of the invention is 5 to 500 mg of active ingredient, and for oral administration is 25 to 5000 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally. Preferred pharmaceutical compositions and medicaments are therefore those adapted for administration such as oral or parenteral administration. Administration in the method of the invention is preferably oral or parenteral administration.

In general it has proved advantageous to administer parenterally amounts of from 0.05 to 100 mg/kg, preferably 0.1 to 10 mg/kg, of body weight per day or to administer orally amounts of from 0.1 to 500 mg/kg, preferably 0.5 to 100 mg/kg, of body weight per day to achieve effective results. Nevertheless, it can at times be necessary to deviate from those dosage rates, and in particular to do so as a function of the nature and body weight of the warm-blooded animals subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples numbered 1 to 17 k illustrate the preparation of the carbonyl compounds of the formula (II) used, according to the invention, as starting substances (Table 1).

Examples 18 to 33 m illustrate the preparation of the alkenecarboxylic acids of the formula (V) used according to the invention (Table 2).

The Examples which then follow, from No. 34, illustrate the preparation of the imidazozole-alkenoic acid amides of the general formula (I) according to the invention (Table 3).

EXAMPLES OF THE PREPARATION OF CARBONYL COMPOUNDS OF THE FORMULA (II)

Example 1

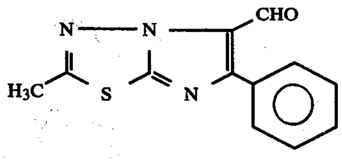

2-Methyl-6-phenyl-imidazo[2,1-b]-1,3,4-thiadiazole-5-carbaldehyde 60 ml of phosphorus oxychloride were added dropwise to 180 ml of dimethylformamide, whilst cooling. A further 400 ml of dimethylformamide, and 130 g (0.6 mole) of 2-methyl-6-phenylimidazo[2,1-b]-1,3,4-thiadiazole were then added and the mixture was warmed to 100° C. for 2 hours. It was poured onto 3 kg of ice, 410 g of 40% strength sodium hydroxide solution were added and the mixture was heated rapidly to 90° C. After 5 minutes, it was cooled and the product was filtered off. Yield: 132 g (90% of theory) of melting point 152° to 153° C.

The examples in Table 1 which follows were prepared analogously by reacting in each case equivalent amounts of the reactants.

TABLE 1

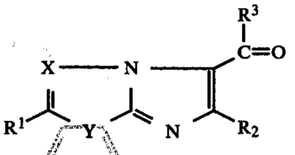

| Example No. | X | Y | $R^1$ | $R^2$ | $R^3$ | Melting point °C. | Yield % of theory |
|---|---|---|---|---|---|---|---|
| 2 | CH | S | H | $C_6H_5$ | H | 128–9 | 25 |
| 3 | N | S | $CF_3$ | $C_6H_5$ | H | 186–8 | 32 |
| 4 | N | S | $C_2H_5$ | $C_6H_5$ | H | 101–2 | 28 |
| 5 | N | S | $CH_2$— 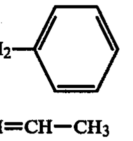 | $C_6H_5$ | H | 140–2 | 40 |
| 6 | N | S | $CH{=}CH{-}CH_3$ | $C_6H_5$ | H | 164–5 | 33 |

TABLE 1-continued
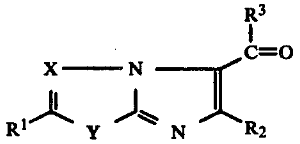
| Example No. | X | Y | $R^1$ | $R^2$ | $R^3$ | Melting point °C. | Yield % of theory |
|---|---|---|---|---|---|---|---|
| 7 | N | S | 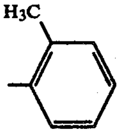 | $C_6H_5$ | H | 149 | 29 |
| 8 | N | S | H | $C_6H_5$ | H | 234–38 | 34 |
| 9 | N | O | $CH_3$ | $C_6H_5$ | H | 165 | 38 |
| 10 | N | NH | $CH_3$ | $C_6H_5$ | H | 270 | 36 |
| 11 | N | S | $CH_3$ | 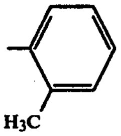 | H | 109–11 | 56 |
| 12 | N | S | $CH_3$ | 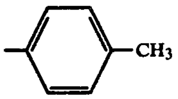 | H | 139–41 | 64 |
| 13 | N | S | $CH_3$ | 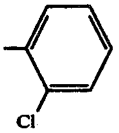 | H | 120–22 | 48 |
| 14 | N | S | $CH_3$ | 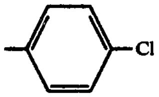 | H | 175–77 | 71 |
| 15 | N | S | $CH_3$ | 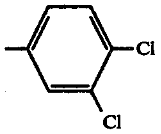 | H | 203–05 | 69 |
| 16 | N | S | $CH_3$ | 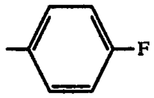 | H | 168–70 | 66 |
| 17 | N | S | $CH_3$ | 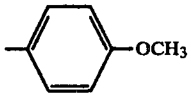 | H | 160–62 | 65 |
| 17a | N | S | $SO_2CH_3$ | $C_6H_5$ | H | 250 | 52 |
| 17b | N | S | $(CH_2)_2—O—C_2H_5$ | $C_6H_5$ | H | 57 | 40 |
| 17c | N | S | $(CH_2)_2—S—CH_3$ | $C_6H_5$ | H | 83 | 66 |
| 17d | N | S | $CO_2n—C_4H_9$ | $C_6H_5$ | H | 74 | 85 |
| 17e | N | S | 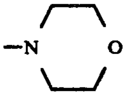 | $C_6H_5$ | H | 180–82 | 83 |

TABLE 1-continued

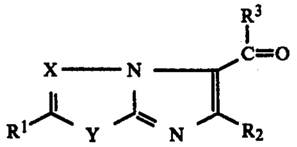

| Example No. | X | Y | $R^1$ | $R^2$ | $R^3$ | Melting point °C. | Yield % of theory |
|---|---|---|---|---|---|---|---|
| 17f | N | S | 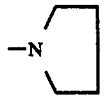 | $C_6H_5$ | H | 200-02 | 95 |
| 17g | N | S | 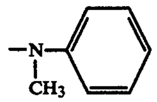 | $C_6H_5$ | H | 142-44 | 87 |
| 17h | N | S | 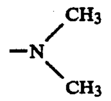 | $C_6H_5$ | H | 167-69 | 96 |
| 17i | N | S | 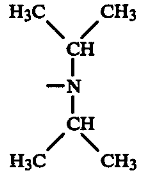 | $C_6H_5$ | H | 128-30 | 91 |
| 17j | N | S | $-CH_3$ | 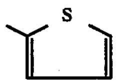 | H | 184-86 | 73 |
| 17k | N | S | $-CH_3$ | 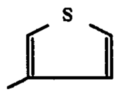 | H | 181-83 | 95 |

EXAMPLES OF THE PREPARATION OF ALKENOIC ACIDS OF THE FORMULA (V)

EXAMPLE 18

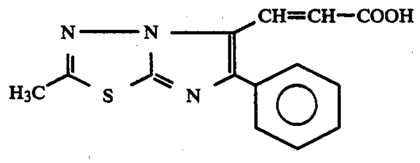

90 g of 2-methyl-6-phenyl-imidazo[2,1-b]-1,3,4-thiadiazole-5-carbaldehyde, 60 g of malonic acid and 3 ml of piperidine in 95 ml of pyridine were boiled under reflux for 10 hours. The mixture was cooled to 5° C., stirred at this temperature for 2 hours and filtered. The residue was washed with water and dried. 92 g (84% of theory) of β-(2-methyl-6-phenyl-imidazo[2,1-b]-1,3,4-thiadiazol-5-yl)-propenoic acid of melting point 278°-280° C. (decomposition) were obtained.

The Examples in the following table were prepared analogously by reacting in each case equivalent amounts of the reactants.

TABLE 2

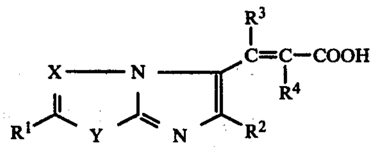

| Example No. | X | Y | $R^1$ | $R^2$ | $R^3$ | $R^4$ | Solvent (for recrystallisation) | Melting point °C. | Yield % of theory |
|---|---|---|---|---|---|---|---|---|---|
| 19 | CH | S | H | $C_6H_5$ | H | H | DMF | 260-1 | 45 |
| 20 | N | S | $CF_3$ | $C_6H_5$ | H | H | Ethanol DMF | 340-2 | 77 |

TABLE 2-continued

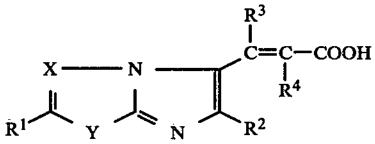

| Example No. | X | Y | $R^1$ | $R^2$ | $R^3$ | $R^4$ | Solvent (for recrystallisation) | Melting point °C. | Yield % of theory |
|---|---|---|---|---|---|---|---|---|---|
| 21 | N | S | $C_2H_5$ | $C_6H_5$ | H | H | Ethanol DMF | 270–2 | 81 |
| 22 | N | S | 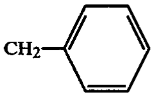 | $C_6H_5$ | H | H | Ethanol DMF | 274–6 | 66 |
| 23 | N | S | $CH{=}CH{-}CH_3$ | $C_6H_5$ | H | H | Ethanol DMF | 278–80 | 24 |
| 24 | N | S | 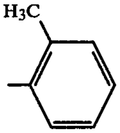 | $C_6H_5$ | H | H | Ethanol DMF | 297–300 | 53 |
| 25 | N | S | H | $C_6H_5$ | H | H | Ethanol DMF | 272–3 | 46 |
| 26 | N | S | $CH_3$ | $C_6H_5$ | H | $CH_3$ | Ethanol DMF | 298–300 | 79.5 |
| 27 | N | S | $CH_3$ | 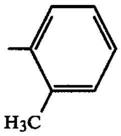 | H | H | Ethanol DMF | 251–53 | 49 |
| 28 | N | S | $CH_3$ | 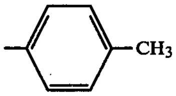 | H | H | Ethanol DMF | 260–62 | 58 |
| 29 | N | S | $CH_3$ | 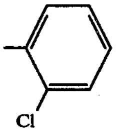 | H | H | Ethanol DMF | 235–37 | 63 |
| 30 | N | S | $CH_3$ | 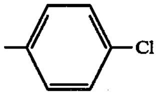 | H | H | Ethanol DMF | 272–74 | 75 |
| 31 | N | S | $CH_3$ | 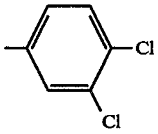 | H | H | Ethanol DMF | 255–57 | 81 |
| 32 | N | S | $CH_3$ | 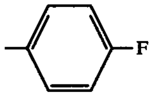 | H | H | Ethanol DMF | 273–75 | 58 |
| 33 | N | S | $CH_3$ | 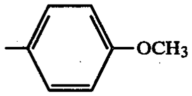 | H | H | Ethanol DMF | 279–81 | 62 |

TABLE 2-continued

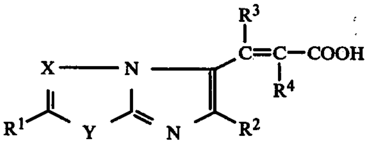

| Example No. | X | Y | $R^1$ | $R^2$ | $R^3$ | $R^4$ | Solvent (for recrystallisation) | Melting point °C. | Yield % of theory |
|---|---|---|---|---|---|---|---|---|---|
| 33a | N | S | 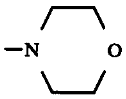 | $C_6H_5$ | H | H | Ethanol,DMF | 272–74 | 85 |
| 33b | N | S | 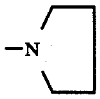 | $C_6H_5$ | H | H | Ethanol,DMF | >280 | 73 |
| 33c | N | S | 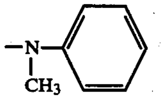 | $C_6H_5$ | H | H | Ethanol,DMF | 230–32 | 81 |
| 33d | N | S | 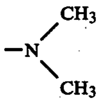 | $C_6H_5$ | H | H | Ethanol,DMF | 288–90 | 80 |
| 33e | N | S | $-CH_3$ | 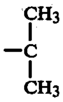 | H | H | Ethanol,DMF | 245–47 | 20 |
| 33f | N | S | 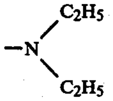 | $C_6H_5$ | H | H | Ethanol,DMF | 225–27 | 60 |
| 33g | N | S | 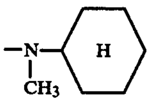 | $C_6H_5$ | H | H | Ethanol,DMF | 248–50 | 58 |
| 33h | N | S | 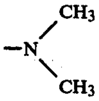 | $C_6H_5$ | H | H | Ethanol,DMF | 243–45 | 57 |
| 33i | N | S | 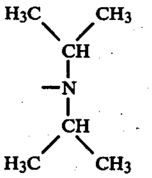 | $C_6H_5$ | H | H | Ethanol,DMF | 225–27 | 93 |
| 33j | N | S | $-CH_3$ | $-CH_3$ | H | H | Ethanol,DMF | 260–62 | 50 |
| 33k | N | S | $-CH_3$ | 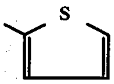 | H | H | Ethanol,DMF | >280 | 78 |
| 33l | N | S | $-CH_3$ | 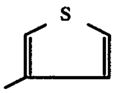 | H | H | Ethanol,DMF | >280 | 73 |

TABLE 2-continued

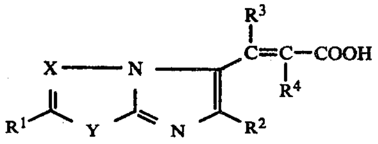

| Example No. | X | Y | $R^1$ | $R^2$ | $R^3$ | $R^4$ | Solvent (for recrystallisation) | Melting point °C. | Yield % of theory |
|---|---|---|---|---|---|---|---|---|---|
| 33m | N | S | $-CH_3$ | $C_6H_5$ | H | H | Ethanol,DMF | 328 | 50 |

The compound of Example 26 of Table 2 was obtained by boiling 15 g of α-methyl-β-(2-methyl-6-phenylimidazo[2,1-b]-1,3,4-thiadiazol-5-yl-propenoic acid ethyl ester, 2.8 g of potassium hydroxide, 200 ml of ethanol and 20 ml of water under reflux for 1 hour. The mixture was cooled, and concentrated in vacuo. The residue was dissolved in 300 ml of water and the solution was filtered. The filtrate was acidified with concentrated hydrochloric acid and the precipitate was filtered off and recrystallised from dimethylformamide. After drying, α-methyl-β-(2-methyl-6-phenylimidazo[2,1-b]-1,3,4-thiadiazol-5-yl)-propenoic acid of melting point 298° to 300° C. (yield: 79.5% of theory) was obtained.

Example 34

(Process variant (b))

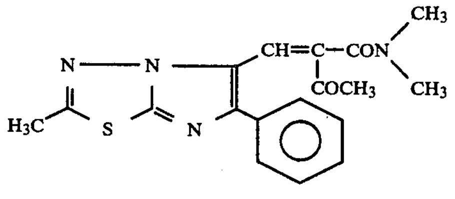

0.03 mole of 2-methyl-6-phenylimidazo[2,1-b]-1,3,4-thiadiazol-5-carbaldehyde, 0.1 mole (13.0 g) of acetoacetic acid dimethylamide and 0.6 ml of piperidine were heated to 120° C. for 4 hours. The mixture was then cooled and the precipitate formed was recrystallised from 30 ml of ethyl acetate. After drying, α-acetyl-β-(2-methyl-6-phenyl-imidazo[2,1-b]-1,3,4-thiadiazol-5-yl)-propenoic acid dimethylamide of melting point 185° to 187° C. was obtained.

Yield: 43% of theory.

Example 35

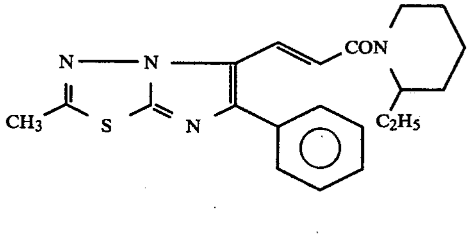

N-[β-(2-Methyl-6-phenyl-imidazo[2,1-b]-1,3,4-thiadiazol-5-yl)-propenoyl]-2-ethyl-piperidine 143 g (0.5 mole) of β-(2-methyl-6-phenyl-imidazo[2,1-b]-1,3,4-thiadiazol-5-yl)-propenoic acid were suspended in 1.5 liters of absolute toluene at 60° to 70° C. 50 ml of thionyl chloride were added dropwise, a clear solution resulting. The solution was then heated under reflux for 2 hours and subsequently cooled to room temperature. 220 ml (1.5 moles) of 2-ethylpiperidine were next added dropwise and the mixture was boiled under reflux for one hour. The cooled mixture was filtered (the residue was discarded) and the filtrate was extracted twice with 300 ml of water. The toluene phase was dried over sodium sulphate and filtered and the filtrate was concentrated by distillation. The residue was recrystallised from 400 ml of ethyl acetate.

Yield: 115 g (60% of theory) of melting point 143° to 144° C.

Example 36

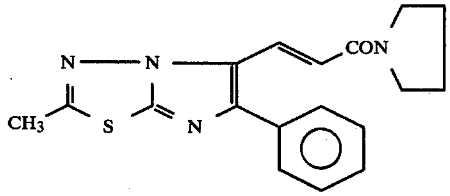

N-[β-(2-Methyl-6-phenylimidazo[2,1-b]-1,3,4-thiadiazol-5-yl)]-propenoylpyrrolidine 0.6 g of sodium hydride (80% in oil) were added to 30 ml of absolute benzene. 5.5 g of diethylphosphonoacetic acid pyrrolidide were then added dropwise, the temperature being kept at 20° C. After the mixture had been stirred at room temperature for 1 hour, a further 40 ml of absolute benzene were added, 4.8 g of 2-methyl-6-phenylimidazo[2,1-b]-1,3,4-thiadiazole-5-carbaldehyde were added in portions and the mixture was boiled under reflux for 1 hour. It was then cooled, and water was added to the crystal sludge. The precipitate was filtered off and recrystallised from 2-propanol.

Yield: 48% of theory; melting point: 210° to 211° C.

The Examples in the following table were prepared analogously to the indicated Examples by reacting in each case equivalent amounts of the reactants.

TABLE 3

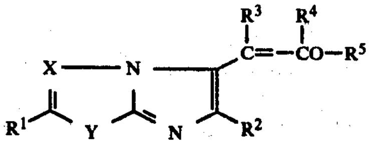

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 37 | N | S | $CH_3$ | $C_6H_5$ | H | H | 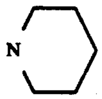 | ethyl acetate | 188–91 | 62 | 35 |
| 38 | N | S | $CH_3$ | $C_6H_5$ | H | H | 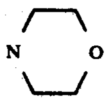 | ethyl acetate | 217–19 | 54 | 36 |
| 39 | N | S | $CH_3$ | $C_6H_5$ | H | H | 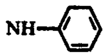 | ethyl acetate | 242–43 | 46 | 35 |
| 40 | N | S | $CH_3$ | $C_6H_5$ | H | H | 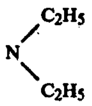 | ethyl acetate | 154–5 | 57 | 35 |
| 41 | N | S | $CH_3$ | $C_6H_5$ | H | H | 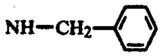 | ethyl acetate | 194–6 | 49 | 35 |
| 42 | N | S | $CH_3$ | $C_6H_5$ | H | H | 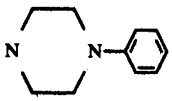 | ethyl acetate | 196–7 | 54 | 35 |
| 43 | N | S | $CH_3$ | $C_6H_5$ | H | H | 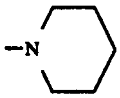 | ethyl acetate | 148–50 | 49 | 35 |
| 44 | N | S | $CH_3$ | $C_6H_5$ | H | H | 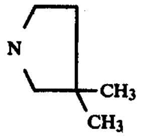 | ethyl acetate | 206 | 58 | 35 |
| 45 | N | S | $CH_3$ | $C_6H_5$ | H | H | 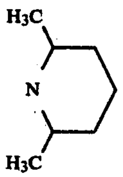 | ethyl acetate | 151 | 59 | 35 |
| 46 | N | S | $CH_3$ | $C_6H_5$ | H | H | 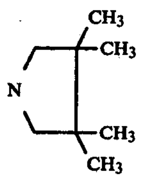 | 2-propanol | 258–9 | 28 | 35 |

TABLE 3-continued

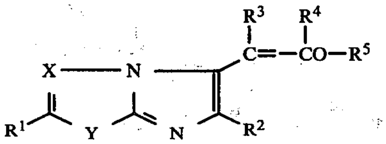

| Example No. | X | Y | R1 | R2 | R3 | R4 | R5 | Solvent (for crystalisation) | Melting point °C. | Yield % of theory | analogous to Example |
|---|---|---|---|---|---|---|---|---|---|---|---|
| 47 | N | S | $CH_3$ | $C_6H_5$ | H | H | 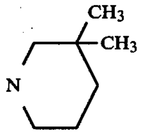 | ethyl acetate | 138–40 | 61 | 35 |
| 48 | N | S | $CH_3$ | $C_6H_5$ | H | H | 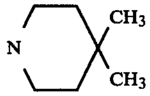 | 2-propanol | 238–40 | 64 | 35 |
| 49 | N | S | $CH_3$ | $C_6H_5$ | H | H | 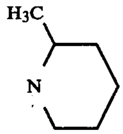 | ethyl acetate | 170–1 | 46 | 36 |
| 50 | CH | S | H | $C_6H_5$ | H | H | 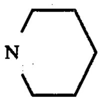 | ethyl acetate | 175–6 | 49 | 35 |
| 51 | N | S | $CF_3$ | $C_6H_5$ | H | H | 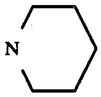 | ethyl acetate | 202–4 | 68 | 35 |
| 52 | N | S | $CF_3$ | $C_6H_5$ | H | H | 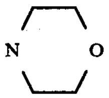 | ethyl acetate | 248–51 | 62 | 35 |
| 53 | N | S | $CF_3$ | $C_6H_5$ | H | H | 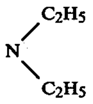 | 2-propanol | 144–7 | 55 | 36 |
| 54 | N | S | $CH_3$ | $C_6H_5$ | H | H | 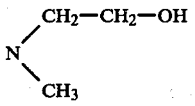 | ethyl acetate | 187–8 | 47 | 35 |
| 55 | N | S | $CH_3$ | $C_6H_5$ | H | H | 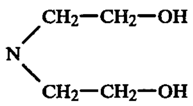 | ethyl acetate | 179–80 | 49 | 35 |
| 56 | N | S | $CH_3$ | $C_6H_5$ | H | H | 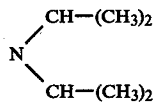 | ethyl acetate | 194–6 | 58 | 35 |
| 57 | N | S | $CH_3$ | $C_6H_5$ | H | H | 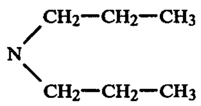 | ethyl acetate | 168–71 | 61 | 35 |

TABLE 3-continued

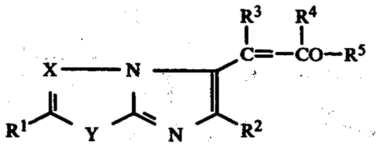

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 58 | N | S | $CH_3$ | $C_6H_5$ | H | H | 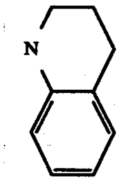 | ethanol | 203–4 | 62 | 35 |
| 59 | N | S | $CH_3$ | $C_6H_5$ | H | H | 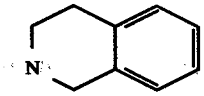 | ethanol | 155–60 | 49 | 35 |
| 60 | N | S | $C_2H_5$ | $C_6H_5$ | H | H | 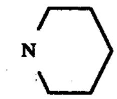 | ethyl acetate | 181–2 | 54 | 36 |
| 61 | N | S | $C_2H_5$ | $C_6H_5$ | H | H | 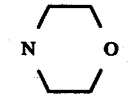 | ethyl acetate | 180–2 | 54 | 36 |
| 62 | N | S | $C_2H_5$ | $C_6H_5$ | H | H | 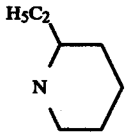 | ethyl acetate | 100–4 | 62 | 35 |
| 63 | N | S | $CH_3$ | $C_6H_5$ | H | H | 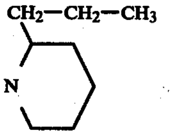 | ethyl acetate | Oil | 24 | 35 |
| 64 | N | S | $CH_3$ | $C_6H_5$ | H | H | 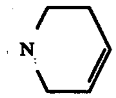 | ethyl acetate | 218–9 | 52 | 35 |
| 65 | N | S | $CH_3$ | $C_6H_5$ | H | H | 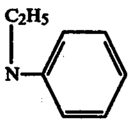 | ethyl acetate | 237–9 | 65 | 35 |
| 66 | N | S | $CH_2-$ | $C_6H_5$ | H | H | 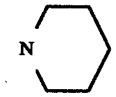 | ethyl acetate | 155 | 24 | 36 |
| 67 | N | S | $CH_2-$ | $C_6H_5$ | H | H | 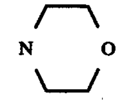 | ethyl acetate | 160–3 | 42 | 36 |

TABLE 3-continued

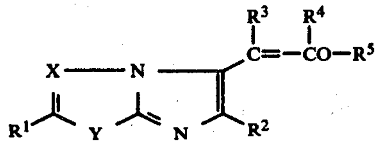

| Example No. | X | Y | R¹ | R² | R³ | R⁴ | R⁵ | Solvent (for crystallisation) | Melting point °C. | Yield % of theory | analogous to Example |
|---|---|---|---|---|---|---|---|---|---|---|---|
| 68 | N | S | $CH_2$— | $C_6H_5$ | H | H | 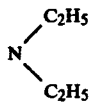 | ethyl acetate | 124–5 | 48 | 36 |
| 69 | N | S | H | $C_6H_5$ | H | H | 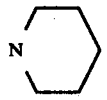 | ethyl acetate | 183–5 | 61 | 36 |
| 70 | N | S | — | $C_6H_5$ | H | H | 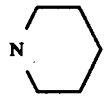 | ethyl acetate | 228–30 | 52 | 36 |
| 71 | N | S | $CH{=}CH{-}CH_3$ | $C_6H_5$ | H | H | 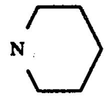 | ethyl acetate | 216–8 | 54 | 36 |
| 72 | N | S | H | $C_6H_5$ | H | H | 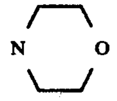 | ethyl acetate | 222–3 | 61 | 36 |
| 73 | N | S | H | $C_6H_5$ | H | H | 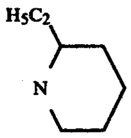 | ethyl acetate | 160–1 | 42 | 35 |
| 74 | N | S | — | $C_6H_5$ | H | H | 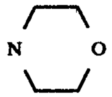 | ethyl acetate | 235–6 | 42 | 36 |
| 75 | N | S | 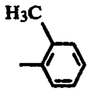 | $C_6H_5$ | H | H | 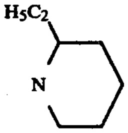 | ethyl acetate | 84–8 | 55 | 35 |
| 76 | N | S | $CH{=}CH{-}CH_3$ | $C_6H_5$ | H | H | 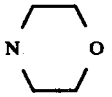 | ethyl acetate | 188–90 | 42 | 36 |
| 77 | N | S | $CH_3$ | $C_6H_5$ | H | $CH_3$ | 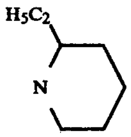 | ethyl acetate | 109–10 | 29 | 35 |

TABLE 3-continued

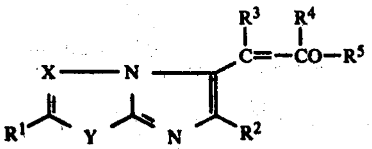

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 78 | N | S | $CH_3$ | $C_6H_5$ | H | $CH_3$ | 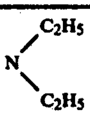 | ethyl acetate | 129–30 | 49 | 35 |
| 79 | N | S | $CH_3$ | $C_6H_5$ | H | $CH_3$ | 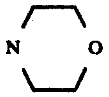 | ethyl acetate | 135–8 | 49 | 35 |
| 80 | N | S | $CH_3$ | 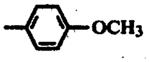 | H | H | 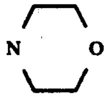 | ethyl acetate | 190–92 | 52 | 35 |
| 81 | N | S | $CH_3$ | 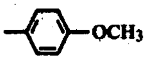 | H | H | 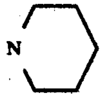 | ethyl acetate | 210–12 | 42 | 35 |
| 82 | N | S | $CH_3$ | 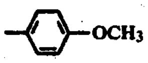 | H | H | 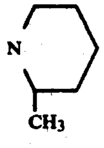 | ethyl acetate | 135–37 | 53 | 35 |
| 83 | N | S | $CH_3$ | 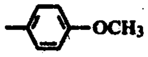 | H | H | 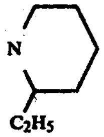 | ethyl acetate | 83–85 | 49 | 35 |
| 84 | N | S | $CH_3$ | 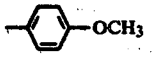 | H | H | 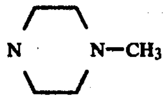 | ethyl acetate | 166–68 | 52 | 35 |
| 85 | N | S | $CH_3$ | 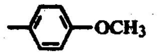 | H | H | 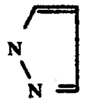 | toluene | 223–25 | 67 | 35 |
| 86 | N | S | $CH_3$ | 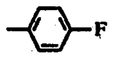 | H | H | 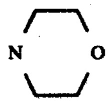 | ethyl acetate | 184–86 | 25 | 36 |
| 87 | N | S | $CH_3$ | 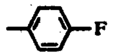 | H | H | 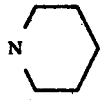 | ethyl acetate | 173–75 | 48 | 36 |

TABLE 3-continued

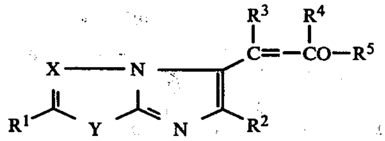

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 88 | N | S | $CH_3$ | 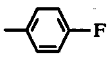 | H | H | 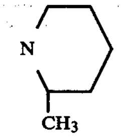 | ethyl acetate | 155–57 | 51 | 35 |
| 89 | N | S | $CH_3$ | 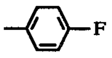 | H | H | 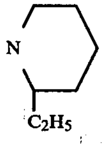 | ethyl acetate | 135–37 | 63 | 35 |
| 90 | N | S | $CH_3$ | 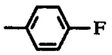 | H | H | 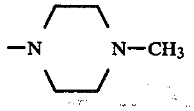 | ethyl acetate | 171–73 | 45 | 35 |
| 91 | N | S | $CH_3$ | 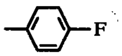 | H | H | 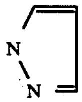 | ethyl acetate | 195–97 | 58 | 35 |
| 92 | N | S | $CH_3$ | 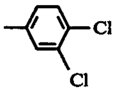 | H | H | 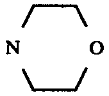 | ethyl acetate | 197–99 | 62 | 35 |
| 93 | N | S | $CH_3$ | 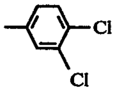 | H | H | 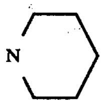 | ethyl acetate | 155–57 | 51 | 36 |
| 94 | N | S | $CH_3$ | 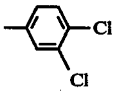 | H | H | 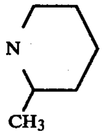 | ethyl acetate | 158–60 | 46 | 35 |
| 95 | N | S | $CH_3$ | 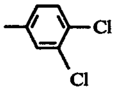 | H | H | 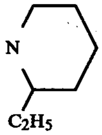 | ethyl acetate | 117–19 | 49 | 35 |
| 96 | N | S | $CH_3$ | 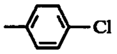 | H | H | 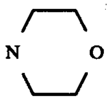 | ethyl acetate | 176–78 | 49 | 35 |
| 97 | N | S | $CH_3$ | 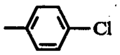 | H | H | 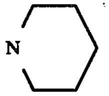 | ethyl acetate | 180–82 | 57 | 36 |

TABLE 3-continued
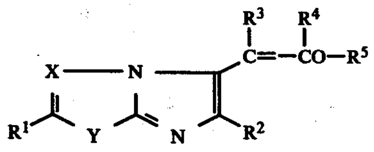
| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 98 | N | S | $CH_3$ | 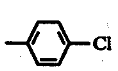 | H | H | 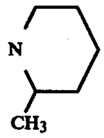 | ethyl acetate | 140–42 | 54 | 35 |
| 99 | N | S | $CH_3$ | 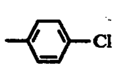 | H | H | 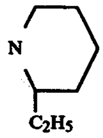 | ethyl acetate | 125–27 | 48 | 35 |
| 100 | N | S | $CH_3$ | 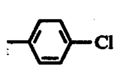 | H | H | 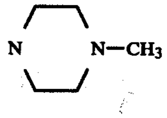 | ethyl acetate | 128–30 | 55 | 35 |
| 101 | N | S | $CH_3$ | 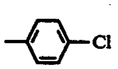 | H | H | 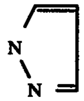 | ethyl acetate | 238–40 | 29 | 35 |
| 102 | N | S | $CH_3$ | 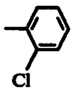 | H | H | 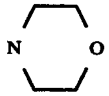 | ethyl acetate | 210–12 | 25 | 36 |
| 103 | N | S | $CH_3$ | 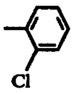 | H | H | 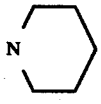 | ethyl acetate | 160–62 | 29 | 36 |
| 104 | N | S | $CH_3$ | 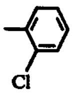 | H | H | 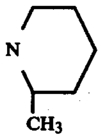 | ethyl acetate | 138–40 | 31 | 35 |
| 105 | N | S | $CH_3$ | 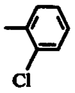 | H | H | 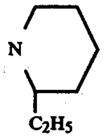 | ethyl acetate | 145–47 | 48 | 35 |
| 106 | N | S | $CH_3$ | 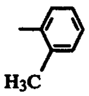 | H | H | 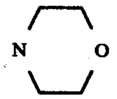 | ethyl acetate | 189–91 | 49 | 36 |

TABLE 3-continued

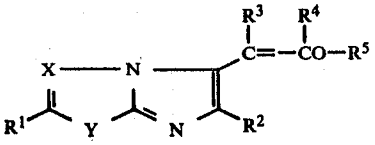

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 107 | N | S | $CH_3$ | 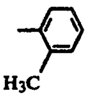 | H | H | 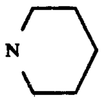 | ethyl acetate | 178–80 | 44 | 36 |
| 108 | N | S | $CH_3$ | 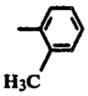 | H | H | 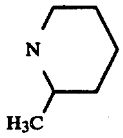 | ethyl acetate | 136–38 | 54 | 35 |
| 109 | N | S | $CH_3$ | 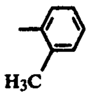 | H | H | 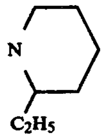 | ethyl acetate | 77–80 | 59 | 35 |
| 110 | N | S | $CH_3$ | 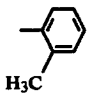 | H | H | 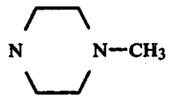 | ethyl acetate | 143–44 | 53 | 35 |
| 111 | N | S | $CH_3$ | 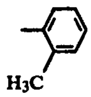 | H | H | 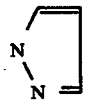 | ethyl acetate | 180–82 | 61 | 35 |
| 112 | N | S | $CH_3$ | 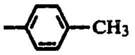 | H | H | 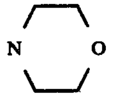 | ethyl acetate | 160–62 | 64 | 36 |
| 113 | N | S | $CH_3$ | 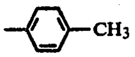 | H | H | 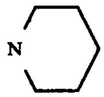 | ethyl acetate | 178–80 | 50 | 36 |
| 114 | N | S | $CH_3$ | 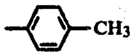 | H | H | 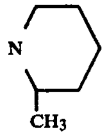 | ethyl acetate | 118–21 | 61 | 35 |
| 115 | N | S | $CH_3$ | 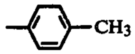 | H | H | 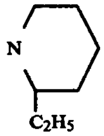 | ethyl acetate | 125–27 | 42 | 35 |
| 116 | N | S | $CH_3$ | $C_6H_5$ | H | H | $NHC_4H_9$ | ethyl acetate | 126 | 52 | 35 |

TABLE 3-continued

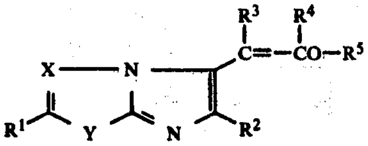

| Example No. | X | Y | R¹ | R² | R³ | R⁴ | R⁵ | Solvent (for crystallisation) | Melting point °C. | Yield % of theory | analogous to Example |
|---|---|---|---|---|---|---|---|---|---|---|---|
| 117 | N | S | $CH_3$ | $C_6H_5$ | H | H | 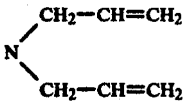 | ethyl acetate | 135 | 60 | 35 |
| 118 | N | S | $CH_3$ | $C_6H_5$ | H | H | 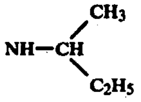 | ethyl acetate | 200 | 71 | 35 |
| 119 | N | S | $CH_3$ | $C_6H_5$ | H | H | 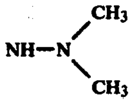 | ethyl acetate | 201 | 47 | 35 |
| 120 | N | S | $CH_3$ | $C_6H_5$ | H | H | $NH_2$ | ethyl acetate | 260-1 | 47 | 35 |
| 121 | N | S | $CH_3$ | $C_6H_5$ | H | CN | $NH_2$ | ethyl acetate | 195-8 | 80 | 34 |
| 122 | N | S | $CH_3$ | $C_6H_5$ | H | CN | 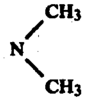 | ethyl acetate | 199-201 | 65 | 34 |
| 123 | N | S | $CH_3$ | $C_6H_5$ | H | H | 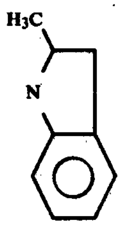 | ethyl acetate | 185-6 | 32 | 35 |
| 124 | N | S | $CH_3$ | $C_6H_5$ | H | CN | 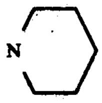 | ethyl acetate | 237-8 | 75 | 34 |
| 125 | N | S | $CH_3$ | $C_6H_5$ | H | H | 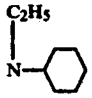 | ethyl acetate | 170-1 | 45 | 35 |
| 126 | N | S | $CH_3$ | $C_6H_5$ | H | H | 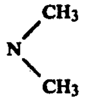 | ethyl acetate | 215 | 54 | 35 |
| 127 | N | S | $CH_3$ | $C_6H_5$ | H | H | 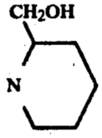 | ethyl acetate | 210 | 39 | 35 |

TABLE 3-continued

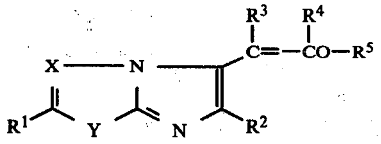

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 128 | N | S | $CH_3$ | $C_6H_5$ | H | H | 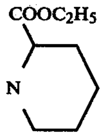 | ethyl acetate | 166 | 28 | 35 |
| 129 | N | S | $CH_3$ | $C_6H_5$ | H | H | 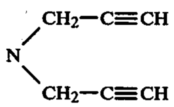 | ethyl acetate | 277 | 55 | 35 |
| 130 | N | S | $CH_3$ | $C_6H_5$ | H | H | 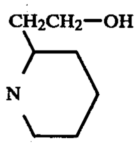 | ethyl acetate | 219 | 43 | 35 |
| 131 | N | S | $CH_3$ | $C_6H_5$ | H | H | 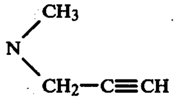 | ethyl acetate | 230-31 | 61 | 35 |
| 132 | N | S | $CH_3$ | $C_6H_5$ | H | H | 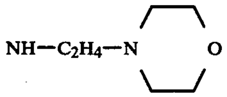 | ethyl acetate | 110 | 29 | 35 |
| 133 | N | O | $CH_3$ | $C_6H_5$ | H | H | 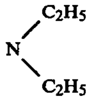 | ethyl acetate | 168-70 | 41 | 36 |
| 134 | N | NH | $CH_3$ | $C_6H_5$ | H | H | 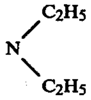 | dimethylformamide | 270-72 | 18 | 36 |
| 135 | N | S | 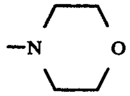 | $C_6H_5$ | H | H | 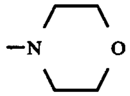 | isopropanol | 203-05 | 66 | 35 |
| 136 | N | S | 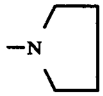 | $C_6H_5$ | H | H | 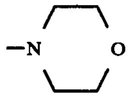 | isopropanol | 288-90 | 83 | 35 |
| 137 | N | S | 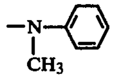 | $C_6H_5$ | H | H | 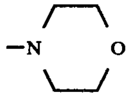 | isopropanol | 163-65 | 61 | 35 |
| 138 | N | S | $-CH_3$ | $-CH_3$ | H | H | 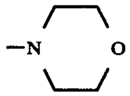 | isopropanol | 130-32 | 19 | 35 |

TABLE 3-continued

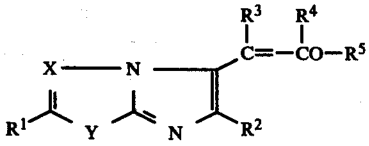

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 139 | N | S | 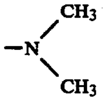 | $C_6H_5$ | H | H | 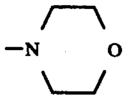 | isopropanol | 233–35 | 79 | 35 |
| 140 | N | S | 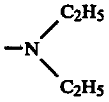 | $C_6H_5$ | H | H | 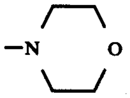 | isopropanol | 133–35 | 70 | 35 |
| 141 | N | S | 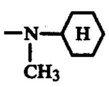 | $C_6H_5$ | H | H | 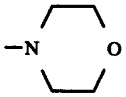 | isopropanol | 125–27 | 71 | 35 |
| 142 | N | S | 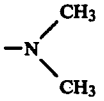 | $C_6H_5$ | H | H | 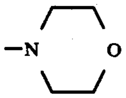 | isopropanol | 133–35 | 80 | 35 |
| 143 | N | S | 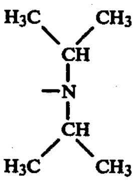 | $C_6H_5$ | H | H | 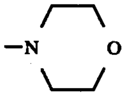 | isopropanol | 188–90 | 54 | 35 |
| 144 | N | S | $-CH_3$ | 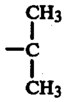 | H | H | 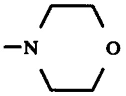 | isopropanol | 240–42 | 58 | 35 |
| 145 | N | S | $-CH_3$ | 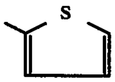 | H | H | 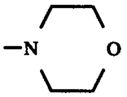 | isopropanol | 185–87 | 70 | 35 |
| 146 | N | S | $-CH_3$ | $-CH_3$ | H | H | 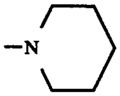 | isopropanol | 100–02 | 26 | 35 |
| 147 | N | S | $-CH_3$ | 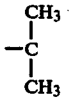 | H | H | 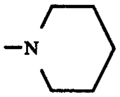 | isopropanol | 135–37 | 19 | 35 |
| 148 | N | S | $-CH_3$ | 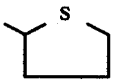 | H | H | 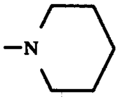 | isopropanol | 185–87 | 48 | 35 |

TABLE 3-continued

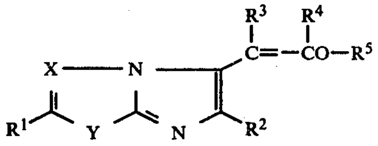

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 149 | N | S | 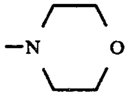 | $C_6H_5$ | H | H | 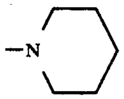 | isopropanol | 205–07 | 22 | 35 |
| 150 | N | S | 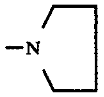 | $C_6H_5$ | H | H | 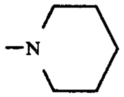 | isopropanol | 275–77 | 75 | 35 |
| 151 | N | S | 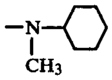 | $C_6H_5$ | H | H | 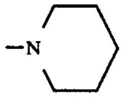 | isopropanol | 143–45 | 54 | 35 |
| 152 | N | S | 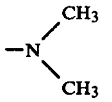 | $C_6H_5$ | H | H | 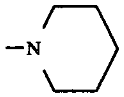 | isopropanol | 198–200 | 85 | 35 |
| 153 | N | S | 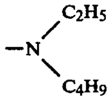 | $C_6H_5$ | H | H | 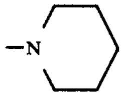 | isopropanol | 113–15 | 63 | 35 |
| 154 | N | S | 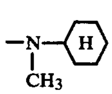 | $C_6H_5$ | H | H | 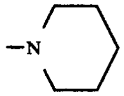 | isopropanol | 170–72 | 23 | 35 |
| 155 | N | S | 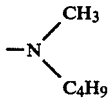 | $C_6H_5$ | H | H | 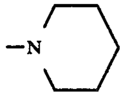 | isopropanol | 123–25 | 88 | 35 |
| 156 | N | S | 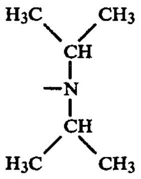 | $C_6H_5$ | H | H | 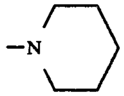 | Isopropanol | 170–72 | 84 | 35 |
| 157 | N | S | $-CH_3$ | 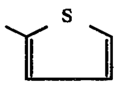 | H | H | 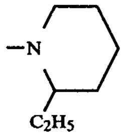 | Isopropanol | 140–42 | 74 | 35 |
| 158 | N | S | 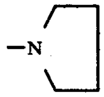 | $C_6H_5$ | H | H | 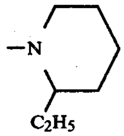 | Isopropanol | 165–67 | 76 | 35 |

TABLE 3-continued
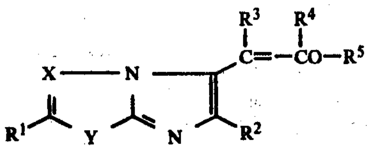
| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 159 | N | S | 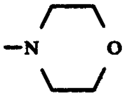 | $C_6H_5$ | H | H | 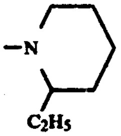 | Isopropanol | 175-77 | 56 | 35 |
| 160 | N | S | 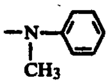 | $C_6H_5$ | H | H | 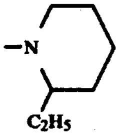 | Isopropanol | 155-57 | 85 | 35 |
| 161 | N | S | 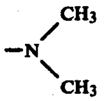 | $C_6H_5$ | H | H | 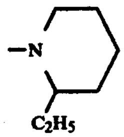 | Isopropanol | 143-45 | 86 | 35 |
| 162 | N | S | 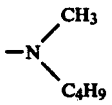 | $C_6H_5$ | H | H | 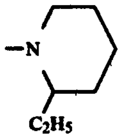 | Isopropanol | 118-20 | 56 | 35 |
| 163 | N | S | $-CH_3$ | 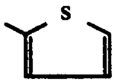 | H | H | 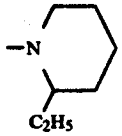 | Isopropanol | 130-32 | 67 | 35 |
| 164 | N | S | $-CH_3$ | 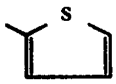 | H | H | 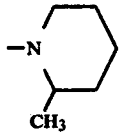 | Isopropanol | 166-68 | 75 | 35 |
| 165 | N | S | $-CH_3$ | 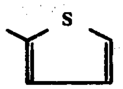 | H | H | 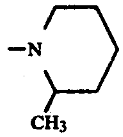 | Isopropanol | 168-70 | 26 | 35 |
| 166 | N | S | 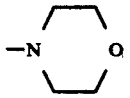 | $C_6H_5$ | H | H | 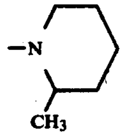 | Isopropanol | 168-70 | 35 | 35 |

TABLE 3-continued
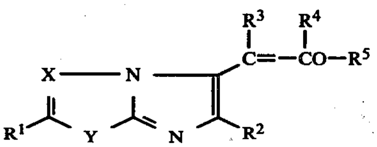
| Example No. | X | Y | R¹ | R² | R³ | R⁴ | R⁵ | Solvent (for crystallisation) | Melting point °C. | Yield % of theory | analogous to Example |
|---|---|---|---|---|---|---|---|---|---|---|---|
| 167 | N | S | 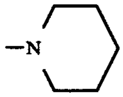 | $C_6H_5$ | H | H | 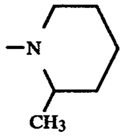 | Isopropanol | 210–12 | 16 | 35 |
| 168 | N | S | 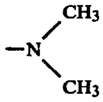 | $C_6H_5$ | H | H | 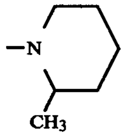 | Isopropanol | 160–62 | 37 | 35 |
| 169 | N | S | 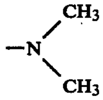 | $C_6H_5$ | H | H | 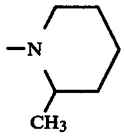 | Isopropanol | 138–40 | 95 | 35 |
| 170 | N | S | 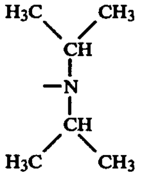 | $C_6H_5$ | H | H | 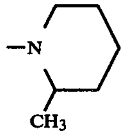 | Isopropanol | 148–50 | 81 | 35 |
| 171 | N | S | 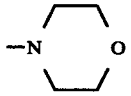 | $C_6H_5$ | H | H | 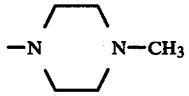 | Isopropanol | 203–05 | 34 | 35 |
| 172 | N | S | 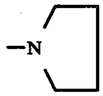 | $C_6H_5$ | H | H | 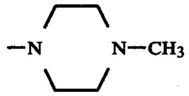 | Isopropanol | 213–15 | 60 | 35 |
| 173 | N | S | 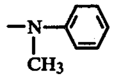 | $C_6H_5$ | H | H | 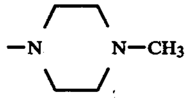 | Isopropanol | 165–67 | 84 | 35 |
| 174 | N | S | 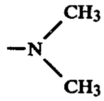 | $C_6H_5$ | H | H | 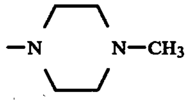 | Isopropanol | 205–07 | 44 | 35 |
| 175 | N | S | 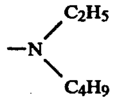 | $C_6H_5$ | H | H | 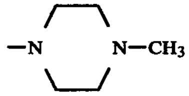 | Isopropanol | 127–29 | 77 | 35 |

TABLE 3-continued
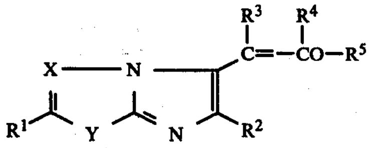
| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 176 | N | S | 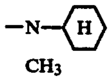 | $C_6H_5$ | H | H | 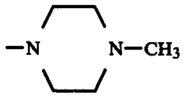 | Isopropanol | 148–50 | 83 | 35 |
| 177 | N | S | 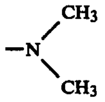 | $C_6H_5$ | H | H | 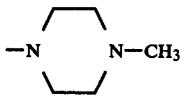 | Isopropanol | 125–27 | 93 | 35 |
| 178 | N | S | 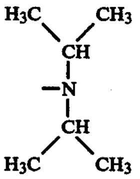 | $C_6H_5$ | H | H | 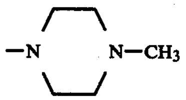 | Isopropanol | 187–89 | 77 | 35 |
| 179 | N | S | $-CH_3$ | 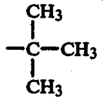 | H | H | 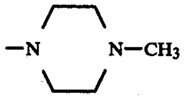 | Isopropanol | 147–49 | 69 | 35 |
| 180 | N | S | $-CH_3$ | 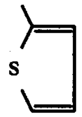 | H | H | 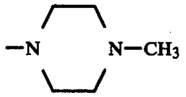 | Isopropanol | 160–62 | 60 | 35 |
| 181 | N | S | $-CH_3$ | 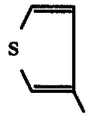 | H | H | 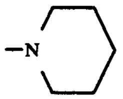 | Isopropanol | 203–05 | 87 | 35 |
| 182 | N | S | 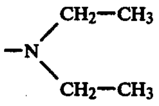 | $C_6H_5$ | H | H | 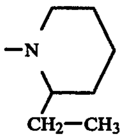 | Isopropanol | 146 | 45 | 35 |
| 183 | N | S | 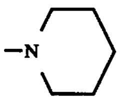 | $C_6H_5$ | H | H | 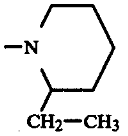 | Isopropanol | 185 | 30 | 35 |
| 184 | N | S | $-CO_2nC_4H_9$ | $C_6H_5$ | H | H | 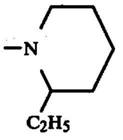 | ethyl acetate | 120 | 50 | 36 |

TABLE 3-continued

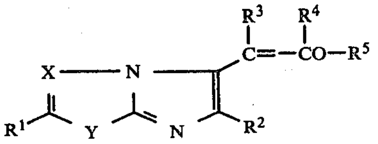

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 185 | N | S | $-COOH$ | $C_6H_5$ | H | H | 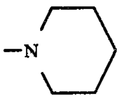 | ethyl acetate | 160 | 80 | 36 |
| 186 | N | S | $-COOH$ | $C_6H_5$ | H | H | 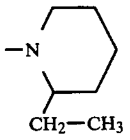 | ethyl acetate | 148 | 80 | 36 |
| 187 | N | S | $-CH_2OH$ | $C_6H_5$ | H | H | 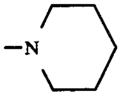 | ethyl acetate | 194 | 48 | 36 |
| 188 | N | S | $-CH_2OH$ | $C_6H_5$ | H | H | 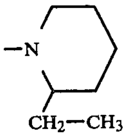 | ethyl acetate | 163 | 50 | 36 |
| 189 | N | S | 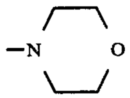 | $C_6H_5$ | H | H | 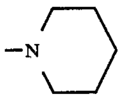 | ethyl acetate | 230 | 60 | 36 |
| 190 | N | S | 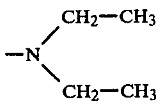 | $C_6H_5$ | H | H | 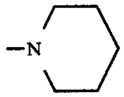 | ethyl acetate | 170 | 65 | 36 |
| 191 | N | S | 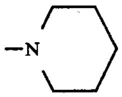 | $C_6H_5$ | H | H | 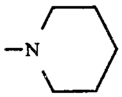 | ethyl acetate | 220 | 60 | 36 |
| 192 | N | S | $-CH_3$ | $C_6H_5$ | H | H | 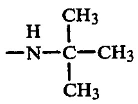 | toluene | 253 | 31 | 35 |
| 193 | N | S | $-CH_3$ | $C_6H_5$ | H | $OC_2H_5$ | 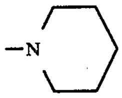 | isopropanol | 178 | 25 | 36 |
| 194 | N | S | $-CO_2CH_3$ | $C_6H_5$ | H | H | 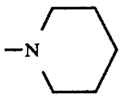 | ethyl acetate | 160 | 55 | 36 |

TABLE 3-continued

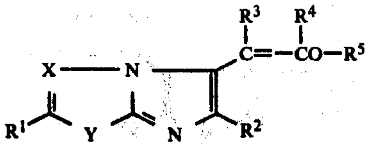

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 195 | N | S | $-CO_2CH_3$ | $C_6H_5$ | H | H | 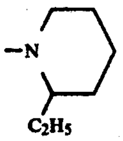 | ethyl acetate | 142 | 50 | 36 |
| 196 | N | S | $-CO_2nC_4H_9$ | $C_6H_5$ | H | H | 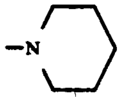 | ethyl acetate | 114 | 60 | 36 |
| 197 | N | S | $-CO_2C_2H_5$ | $C_6H_5$ | H | H | 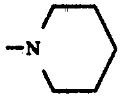 | ethyl acetate | 146 | 80 | 36 |
| 198 | N | S | $-CO_2CH(CH_3)_2$ | $C_6H_5$ | H | H | 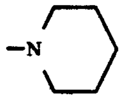 | ethyl acetate | 135 | 90 | 36 |
| 199 | N | S | $-CH_3$ | $C_6H_5$ | H | H | 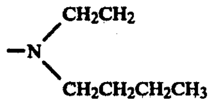 | cyclohexane | 140 | 55 | 35 |
| 200 | N | S | $-CH_3$ | $C_6H_5$ | H | H | 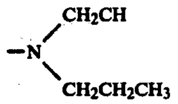 | toluene | 152 | 65 | 35 |
| 201 | N | S | $-CH_3$ | $C_6H_5$ | H | H | 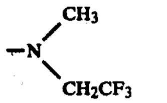 | toluene | 180 | 45 | 35 |
| 202 | N | S | $-CH_3$ | $C_6H_5$ | H | H | 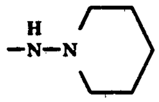 | toluene | 230 | 50 | 35 |
| 203 | N | S | $-CH_3$ | $C_6H_5$ | H | H | 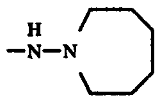 | toluene | 200 | 70 | 35 |
| 204 | N | S | $-CH_3$ | $C_6H_5$ | H | H | 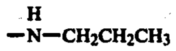 | toluene | 190 | 30 | 35 |
| 205 | N | S | $-CH_3$ | $C_6H_5$ | H | H | 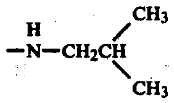 | toluene | 165 | 33 | 35 |

TABLE 3-continued

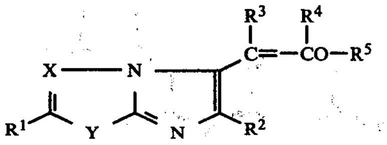

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 206 | N | S | $-(CH_2)_2SCH_3$ | $C_6H_5$ | H | H | 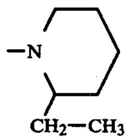 | isopropanol | 96 | 15 | 36 |
| 207 | N | S | $-CH_3$ | $C_6H_5$ | H | H | 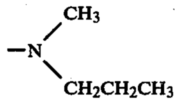 | toluene | 156 | 51 | 35 |
| 208 | N | S | $-CH_3$ | $C_6H_5$ | H | H | 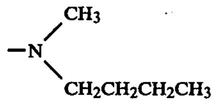 | toluene | 128 | 60 | 35 |
| 209 | N | S | $-CH_3$ | $C_6H_5$ | H | H | 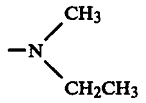 | toluene | 190 | 55 | 35 |
| 210 | N | S | $-CH_3$ | $C_6H_5$ | H | F | 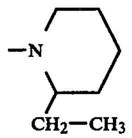 | isopropanol | 130 | 34 | 35 |
| 211 | N | S | $-CH_3$ | $C_6H_5$ | H | H | 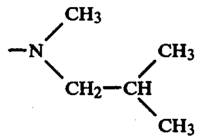 | toluene | 131 | 50 | 35 |
| 212 | N | S | $-CH_3$ | $C_6H_5$ | H | H | 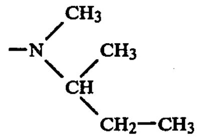 | toluene | 131 | 55 | 35 |
| 213 | N | S | $-CH_3$ | $C_6H_5$ | H | H | 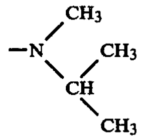 | toluene | 160 | 40 | 35 |
| 214 | N | S | $-CH_3$ | $C_6H_5$ | H | H | 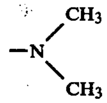 | isopropanol | 215 | 80 | 35 |
| 215 | N | S | $-CH_3$ | $C_6H_5$ | H | H | $NH-CH_2CH_2OCH_3$ | isopropanol | 95 | 67 | 35 |

TABLE 3-continued

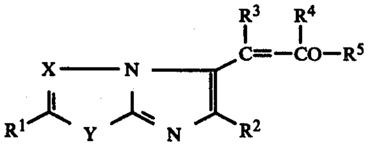

| Example No. | X | Y | $R^1$ | $R^2$ | $R^3$ | $R^4$ | $R^5$ | Solvent (for crystalisation) | Melting point °C. | Yield % of theory | analogous to Example |
|---|---|---|---|---|---|---|---|---|---|---|---|
| 216 | N | S | $-CH_3$ | $C_6H_5$ | H | H | 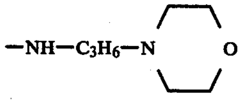 | isopropanol | 153 | 50 | 35 |
| 217 | N | S | $-CH_3$ | $C_6H_5$ | H | H | $-NH-(CH_2)_5-CH_3$ | ethanol | 112 | 75 | 35 |
| 218 | N | S | $-CH_3$ | $C_6H_5$ | H | H | 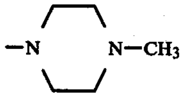 | isopropanol | 167 | 65 | 35 |
| 219 | N | S | $-CH_3$ | $C_6H_5$ | H | CN | 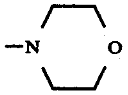 | ethanol | 239 | 78 | 34 |
| 220 | N | NH | $-CH_3$ | $C_6H_5$ | H | H | 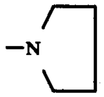 | DMF | ≈280 | 25 | 36 |
| 221 | N | NH | $-CH_3$ | $C_6H_5$ | H | H | 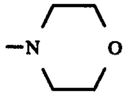 | DMF | ≈280 | 30 | 36 |
| 222 | N | S | $-CH_3$ | $-CH_3$ | H | H | 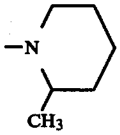 | Isopropanol | 149-51 × HCl | 18 | 35 |
| 223 | N | S | $-CH_3$ | 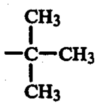 | H | H | 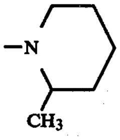 | Isopropanol | 173-75 × HCl | 23 | 35 |
| 224 | N | S | $-CH_3$ | 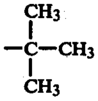 | H | H | 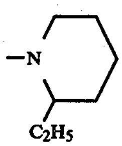 | Isopropanol | 180-82 × HCl | 37 | 35 |
| 225 | N | S | $-CH_3$ | $-CH_3$ | H | H | 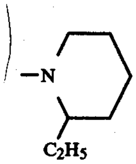 | Isopropanol | 139-41 × HCl | 42 | 35 |

TABLE 3-continued

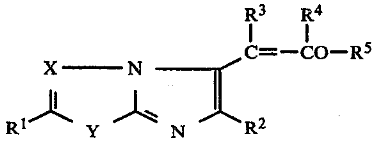

| Example No. | X | Y | $R^1$ | $R^2$ | $R^3$ | $R^4$ | $R^5$ | Solvent (for crystallisation) | Melting point °C. | Yield % of theory | analogous to Example |
|---|---|---|---|---|---|---|---|---|---|---|---|
| 226 | N | S | 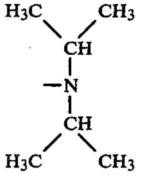 | $-C_6H_5$ | H | H | 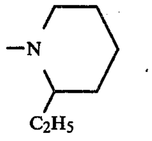 | Isopropanol | 133-35 × HCl | 52 | 35 |
| 227 | N | S | $-CH_3$ | $-CH_3$ | H | H | 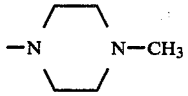 | Isopropanol | 300-02 × HCl | 37 | 35 |
| 228 | N | S | 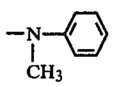 | $C_6H_5$ | H | H | 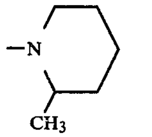 | Isopropanol | 158-60 × HCl | 47 | 35 |

Example 229

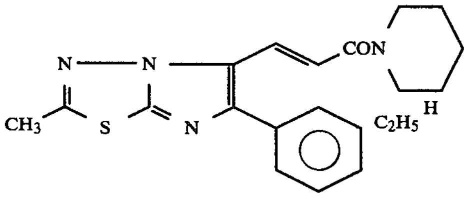

(−)-R-trans-N-[β-(2-Methyl-6-phenyl-imidazo[2,1-b]-1,3,4-thiadiazol-5-yl)-propenoyl]-2-ethyl-piperidine 2 ml of thionyl chloride were added (dropping funnel) to 5.7 g of trans-β-(2-methyl-6-phenyl-imidazo[2,1-b]-1,3,4-thiadiazole-5-yl)-propenoic acid (prepared according to Example 18) in 60 ml of toluene at 65° C. The mixture was boiled under reflux for 2 hours (clear solution). 8 ml of (−)-R-2-ethylpiperidine (H. Frese, Ber. Dtsch. Chem. Ges. 33, 3483 (1900); and H. C. Beyerman et al., Rec. Trac. Chim. Pays-Bas 90, 755 (1971)) were then added dropwise at 40° C. and the mixture was boiled under reflux for a further 60 minutes. It was cooled to room temperature, the precipitate was filtered off and the filtrate was extracted twice with 30 ml of water. The toluene solution was dried over sodium sulphate and concentrated on a rotary evaporator. The residue (8.0 g) was chromatographed on a silica gel column (elution with chloroform). The fractions were collected from the chromatogram and recrystallised from cyclohexane.

Yield: 7.2 g (94% of theory) of melting point 113°-114° C.; specific rotation (in $CHCl_3$) $[\alpha]_{589}^{20} = -34.89°$.

$C_{21}H_{24}N_4OS$ (380.15) Calculated: C 66.3, H 6.4, N 14.7, S 8.4. Found: C 66.0, H 6.4, N 14.6, S 8.7.

Example 230

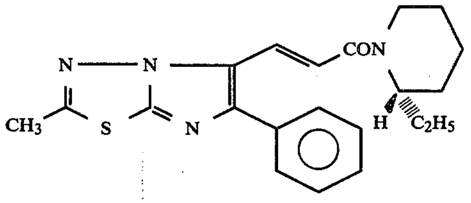

(+)-S-trans-N-[β-(2-Methyl-6-phenyl-imidazo[2,1-b]-1,3,4-thiadiazol-5-yl)-propenoyl]-2-ethyl-piperidine 3 ml of thionyl chloride were added (dropping funnel) to 8.7 of trans-β-(2-methyl-6-phenyl-imidazo[2,1-b]-1,3,4-thiadiazol-5-yl)-propenoic acid (preferred according to Example 18) in 90 ml of toluene at 65° C. The mixture was boiled under reflux for 2 hours (clear solution). 12 g of (+)-S-2-ethylpiperidine (H. Frese, Ber. Dtsch. Chem. Ges. 33, 3483 (1900); and H. C. Beyerman et al., Rec. Trac. Chim. Pays-Bas 90, 755 (1971)) were then added dropwise at 40° C. and the mixture was boiled under reflux for a further 60 minutes. It was cooled to room temperature the precipitate was filtered off and the filtrate was extracted three times with 30 ml of water. The toluene solution was dried over sodium sulphate and concentrated on a rotary evaporator. The residue was recrystallised from cyclohexane.

Yield: 5.0 g (44% of theory) of melting point 112°-113° C.; specific rotation (in $CHCl_3$) $[\alpha]_{589}^{20} = +33.02°$.

$C_{21}H_{24}N_4OS$ (380.15). Calculated: C 66.3, H 6.4, N 14.7, S 8.4. Found: C 65.9, H 6.3, N 14.7, S 8.6.

Among the new imidazoazole-alkenoic acid amide salts of the invention, those salts that are pharmaceutically acceptable are particularly important and are preferred.

The new free imidazoazole-alkenoic acid amides of the general formula (I) and their salts can be interconverted in any suitable manner; methods for such interconversion are known in the art.

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to a warm-blooded animal is converted in the patient's body to the active compound.

What is claimed is:

1. A compound which is an imidazoazole-alkenoic acid amide of the formula

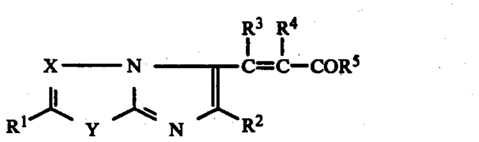

(I)

or a salt thereof, in which

X is N or CH,

Y is S, O, NH or N-alkyl with 1 to 4 carbon atoms, $R^1$ is a hydrogen atom; a straight-chain, branched or cyclic alkyl, alkenyl or alkinyl radical which has up to 6 carbon atoms and is optionally substituted by phenyl, cyano, hydroxyl, fluorine, chlorine or bromine, the carbon chain of the alkyl radical optionally being interrupted by O, S, NH, N-alkyl with 1 to 4 carbon atoms or N-benzyl;

a $SO_n$—$C_1$ to $C_4$ alkyl group, in which n is 0, 1 or 2; a radical of the formula

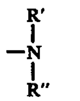

wherein R' and R" are identical or different and each represent a hydrogen atom, a benzyl or phenyl radical or an alkyl radical with 1 to 6 carbon atoms, which is optionally interrupted by O, S or N-$C_1$ to $C_4$ alkyl, or in which R' and R", together with the nitrogen atom, form a 5-membered to 7-membered ring, which optionally contains 1 or 2 identical or different hetero-atoms selected from oxygen, sulphur and nitrogen, the nitrogen optionally being substituted by hydrogen, alkyl with 1 to 4 carbon atoms, phenyl or benzyl; or a radical of the formula COR'", wherein R'" denotes a hydrogen atom, a hydroxyl, alkyl or alkoxy radical with in each case 1 to 6 carbon atoms, a phenoxy or benzyloxy radical, an alkenoxy radical with up to 4 carbon atoms or a radical of the formula

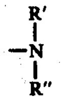

wherein R' and R" have the immediate abovementioned meaning, $R^2$ is hydrogen, a phenyl, naphthyl, furyl, thienyl, pyrimidyl, pyrazinyl, quinolyl, isoquinolyl or pyridyl radical which is optionally substituted by 1, 2 or 3 identical or different substituents selected from alkyl, alkoxy, halogen, nitro, trifluoromethyl and $SO_n$-alkyl, in which n is 0, 1 or 2, the alkyl and alkoxy radicals mentioned each containing 1 to 4 carbon atoms; or a straight-chain, branched or cyclic alkyl, alkenyl or alkinyl radical which has up to 6 carbon atoms, $R^3$ represents a hydrogen atom, a trifluoromethyl radical or an alkyl radical with 1 to 4 carbon atoms, $R^4$ is a hydrogen atom; a cyano group, a fluorine atom, an alkoxy radical with 1 to 4 carbon atoms; a straight-chain or branched alkyl, alkenyl or alkinyl radical with in each case up to 6 carbon atoms, the alkyl radical optionally being substituted by fluorine, chlorine, bromine or cyano and optionally being interrupted by O, S, NH, N-benzyl or N-$C_1$ to $C_4$ alkyl; or a radical of the formula COR'", wherein R'" has the meaning given above in the definition of $R^1$ and can be identical to or different from this substituent and $R^5$ is an amino group of the formula

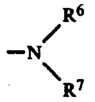

in which (a) $R^6$ denotes a hydrogen atom, a phenyl radical or a straight-chain, branched or cyclic, saturated or unsaturated aliphatic hydrocarbon radical which has up to 10 carbon atoms and is optionally interrupted by O, S, N, N-$C_1$ to $C_4$ alkyl, NH, N-phenyl or N-benzyl and is optionally substitued by hydroxyl, alkoxy, alkyl, fluorine, chlorine, bromine, phenyl, alkoxycarbonyl or dialkylamino with in each case 1 to 4 carbon atoms in the alkyl and alkoxy radicals, the two alkyl radicals, with the N atom, optionally forming a 5-membered to 7-membered ring which is optionally interrupted by O, S, NH or N-$C_1$ to $C_4$ alkyl, and the abovementioned alkyl and phenyl radicals in turn optionally being substituted by fluorine, chlorine, bromine, trifluoromethyl, phenyl, benzyl, alkyl, alkoxy or $SO_2$-alkyl, with in each case 1 to 4 carbon atoms in the alkyl and alkoxy radicals, or (b) $R^6$, together with $R^7$ and with the nitrogen atom, forms a 4-membered to 7-membered ring which optionally contains 1 further hetero-atom selected from oxygen, sulphur and nitrogen, the nitrogen optionally being substituted by hydrogen, $C_1$ to $C_4$ alkyl, phenyl or benzyl, this 4-membered to 7-membered ring being unsubstituted or substituted by 1 to 4 identical or different substituents selected from halogen, trifluoromethyl, phenyl, benzyl, alkyl, hydroxyalkyl, alkoxyalkyl and alkoxycarbonyl with in each case 1 to 4 carbon atoms in the alkyl and alkoxy radicals, this ring optionally being fused onto an aromatic ring which is optionally substituted by fluorine, chlorine, bromine, nitro or hydroxyl, and (c) $R^7$ has the meaning of $R^6$ given immediately above under (a), $R^7$ and $R^6$ being identical or different or (d) one of the two radicals $R^6$ or $R^7$ represents a group of the formula

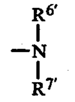

wherein the radicals $R^{6'}$ and $R^{7'}$ have the meanings of $R^6$ and $R^7$ given immediately above under (a) and (b) (hydrazines).

2. A compound according to claim 1 in which

X represents N or CH,

Y represents S, O or NH, $R^1$ and $R^2$ are identical or different and each represent a hydrogen atom, a trifluoromethyl or phenyl radical, an alkyl or alkenyl radical which has up to 6 carbon atoms and is optionally substituted by fluorine, chlorine, hydroxyl, trifluoromethyl or alkyl or alkoxy with in each case 1 or 2 carbon atoms;

represent a pyridyl, thienyl, furyl, naphthyl, pyrimidyl, pyrazinyl, quinolyl or isoquinolyl radical;

represent a radical of the formula

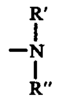

wherein R′ and R″ are identical or different and each represent a hydrogen atom, a benzyl or phenyl radical or a straight-chain, branched or cyclic alkyl radical with up to 6 carbon atoms, the alkyl radicals in turn being optionally interrupted by O, S or N-$C_1$ or $C_2$ alkyl or wherein R′ and R″, together with the nitrogen atom, form a 5-membered to 7-membered ring, which in turn contains 0, 1 or 2 identical or different hetero-atoms selected from oxygen, sulphur and nitrogen, the nitrogen optionally being substituted by hydrogen, alkyl with 1 or 2 carbon atoms, phenyl or benzyl; or represent a radical of the general formula COR‴, wherein R‴ denotes a hydrogen atom, a hydroxyl radical, an alkyl or alkoxy radical with in each case up to 4 carbon atoms, a phenoxy radical or a radical of the formula

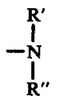

wherein R′ and R″ have the abovementioned meaning, $R^3$ represents a hydrogen atom, a trifluoromethyl radical or an alkyl radical with 1 to 4 carbon atoms, $R^4$ represents a hydrogen atom, an alkyl or alkoxy radical which has in each case 1 to 4 carbon atoms and is optionally interrupted by oxygen and optionally substituted by fluorine, chlorine or cyano, or a cyano or nitro radical, or a radical of the formula COR‴, (wherein R‴ has the meaning given immediately above in the definition of $R^1$ and $R^2$) or $R^4$ represents $SO_n$—$C_1$ to $C_4$ alkyl (in which n is 0 or 2) and $R^5$ represents an amino group of the formula

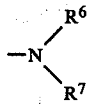

in which (a) $R^6$ denotes a hydrogen atom, a phenyl radical or a straight-chain, branched, cyclic, saturated or unsaturated hydrocarbon radical which has up to 10 carbon atoms, is optionally interrupted by C, S, N, NH, N-phenyl or N-benzyl and is optionally substituted by hydroxyl, alkoxy, fluorine, chlorine bromine, phenyl, alkoxycarbonyl or dialkylamino with in each case 1 to 4 carbon atoms in the alkyl and alkoxy radicals, the two alkyl radicals optionally forming, with the N atom, a 5-membered or 6-membered ring which is optionally interrupted by O, S or NH, and the abovementioned alkyl and phenyl radicals in turn being optionally substituted by fluorine, chlorine, bromine, trifluoromethyl, alkyl, alkoxy or $SO_2$-alkyl with in each case 1 to 4 carbon atoms in the alkyl and alkoxy radicals, or (b) $R^6$, together with $R^7$ and with the nitrogen atom, forms a 4-membered to 7-membered ring which optionally contains 1 or 2 further hetero-atoms selected from oxygen, sulphur and nitrogen, the nitrogen optionally being substituted by hydrogen, $C_1$ or $C_2$ alkyl, phenyl or benzyl, this 4-membered to 7-membered ring being optionally substituted by 1 to 4 identical or different substituents selected from fluorine, chlorine, trifluoromethyl, alkyl, hydroxyalkyl, alkoxyalkyl and alkoxycarbonyl with in each case 1 to 4 carbon atoms in the alkyl and alkoxy radicals, or this ring being optionally fused onto an aromatic ring which is optionally substituted by fluorine, chlorine, nitro or hydroxyl, and (c) $R^7$ has the meaning of $R^6$ given immediately above under (a), $R^7$ and $R^6$ being identical or different, or (d) one of the two radicals $R^6$ or $R^7$ represents a group of the formula

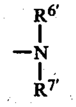

wherein the radicals $R^{6'}$ and $R^{7'}$ have the meaning of $R^6$ and $R^7$ given immediately above under (a) and (b) (hydrazines).

3. A compound according to claim 1 in which X, Y and $R^3$ have the same meanings as in claim 1, $R^1$ and $R^2$ are identical or different and each represent a hydrogen atom or a straight-chain, branched or cyclic alkyl, alkenyl or alkinyl radical, optionally substituted by phenyl, cyano or halogen, the carbon chain of the alkyl radical optionally being interrupted by O, S, NH, N-alkyl or N-aralkyl;

represent a phenyl, naphthyl, furyl, thienyl, pyrimidyl, pyrazinyl, quinolyl, isoquinolyl or pyridyl radical which is optionally substituted by 1, 2 and 3 identical or different substituents selected from alkyl, alkoxy, halogen, nitro, trifluoromethyl and $SO_n$-alkyl (in which n is 0,1 or 2);

represent a $SO_n$-alkyl group (in which n is 0, 1 or 2); or represent a radical of the formula

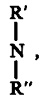

(wherein R′ and R″ are identical or different and each represent a hydrogen atom or an aralykyl or alkyl radical, the alkyl radicals in turn being optionally interrupted by O, S or N-alkyl, or in which R′ and R″, together with the nitrogen atom, form a 5-membered to 7-membered ring, which in turn optionally contains 1 to 2 further hetero-atoms selected from O, S and NH, the nitrogen being optionally substituted by alkyl, aryl or aralkyl, $R^4$ represents a hydrogen atom, a cyano group, a halogen atom or a nitro or $SO_n$-alkyl radical (in which n is 0, 1 or 2);

represents a straight-chain, branched or cyclic alkyl, alkenyl or alkinyl radical, the carbon chain of the alkyl radical optionally being substituted by halogen or cyano and optionally being interrupted by O-, S- or N-alkyl;

or represents a radical of the general formula COR‴, (wherein R‴ denotes a hydrogen atom or an alkyl, alkoxy, alkenyl, alkenoxy or alkinyl radical or denotes a radical of the formula

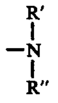

wherein R′ and R″ have the meaning given immediately above in the definition of $R^1$ and $R^2$ and are identical to or different from these radicals), and $R^5$ represents an amino group of the formula

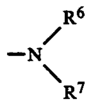

in which (a) $R^6$ denotes a hydrogen atom, a phenyl radical or a straignt-chain, branched, saturated or unsaturated hydrocarbon radical which is optionally interrupted by O—, S—, N—, NH—, N-phenyl or N-benzyl and which is optionally substituted by hydroxyl, halogen, phenyl, alkoxycarbonyl or dialkylamine, the two alkyl radicals optionally forming, together with the N atom, a 5-membered to 7-membered ring which is optionally interrupted by a hetero-atom selected from O, S, NH and N-alkyl, and the abovementioned alkyl and phenyl radicals in turn optionally being substituted by halogen, trifluoromethyl, alkyl, alkoxy or $SO_2$-alkyl, or (b) $R^6$, together with $R^7$ and with the nitrogen atom, forms a 3-membered to 8-membered ring which optionally contains 1 or 2 further heteroatoms selected from oxygen, sulphur and nitrogen, the nitrogen optionally being substituted by alkyl, aryl or aralkyl, or fused onto an aromatic ring, and (c) $R^7$ has the meaning of $R^6$ given immediately above under (a), $R^7$ and $R^6$ being identical or different, or (d) one of the two radicals $R^6$ or $R^7$ represents the group

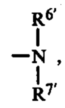

the radicals $R^{6'}$ and $R^{7'}$ having the meaning of $R^6$ and $R^7$ given immediately above under (a) and (b).

4. A compound according to claim 3, in which

X represents N,

Y represents S, O or NH, $R^1$ and $R^2$ are identical or different and each represent a hydrogen atom, a trifluoromethyl radical, an alkyl radical which has 1 to 4 carbon atoms, a phenyl radical which is optionally substituted by fluorine, chlorine, trifluoromethyl or alkyl or alkoxy with in each case 1 to 2 carbon atoms; or represent a pyridyl, thienyl, furyl, naphthyl, pyrimidyl, pyrazinyl, quinolyl or isoquinolyl radical, $R^3$ represents a hydrogen atom, a trifluoromethyl radical or an alkyl radical with 1 to 4 carbon atoms, $R^4$ represents a hydrogen atom, an alkyl radical with 1 to 6 carbon atoms, optionally interrupted by oxygen and optionally substituted by fluorine, chlorine or cyano, or cyano, nitro:

represents a radical of the formula COR‴, wherein R‴ denotes an alkyl or alkoxy radical which has up to 4 carbon atoms; or represents a $SO_n$—$C_1$ to $C_4$ alkyl radical (in which n is 0 or 2), and $R^5$ represents an amino group of the formula

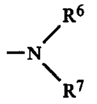

in which (a) $R^6$ denotes a hydrogen atom, a phenyl radical or a straight-chain, branched, saturated or unsaturated hydrocarbon radical which has up to 10 carbon atoms, is optionally interrupted by O, S, N, NH, N-phenyl or N-benzyl and is optionally substituted by hydroxyl, fluorine, chlorine, bromine, phenyl, alkoxycarbonyl or dialkylamine with in each case 1 to 4 carbon atoms in the alkyl and alkoxy radicals, the two alkyl radicals optionally forming, with the N atom, a 5-membered or 6-membered ring which is optionally interrupted by O, S or NH, and the abovementioned alkyl and phenyl radicals in turn being optionally substituted by fluorine, chlorine, bromine, trifluoromethyl, alkyl, alkoxy or $SO_2$-alkyl with in each case 1 to 4 carbon atoms in the alkyl and alkoxy radicals, or (b) $R^6$, together with $R^7$ and with the nitrogen atom, forms a 3-membered to 8-membered ring which optionally contains 1 or 2 further hetero-atoms selected from oxygen, sulphur and nitrogen, the nitrogen optionally being substituted by $C_1$ to $C_4$ alkyl, phenyl or benzyl, or fused onto an aromatic ring which is optionally substituted by fluorine, chlorine, bromine, nitro or hydroxyl, and (c) $R^7$ has the meaning of $R^6$ given immediately above under (a), $R^7$ and $R^6$ being identical or different or (d) one of the two radicals $R^6$ or $R^7$ represents the group

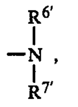

the radicals $R^{6'}$ and $R^{7'}$ having the meaning of $R^6$ and $R^7$ given immediately above under (a) and (b).

5. A compound according to claim 1 in which
X represents N,
Y represents S
$R_1$ represents $CH_3$
$R_2$ represents hydrogen, $C_1$–$C_4$-alkyl, phenyl, optionally substituted by 1 or 2 substituents selected from $CH_3$, Cl, $OCH_3$ and F, furyl, 2- and 3-thienyl, pyridyl, naphthyl, furyl, thienyl, pyrimidyl, pyrazinyl, quinolyl, isoquinolyl or pyridyl which is optionally substituted by 1, 2, or 3 identical or different substituents selected from nitro, trifluoromethyl, fluorine, chlorine, bromine, alkyl, alkoxy and $SO_n$-alkyl (in which n is 0, 1 or 2), hydrogen or $C_1$–$C_4$-alkyl; $R_3$ represents hydrogen, $C_1$–$C_4$-alkyl or $CF_3$, $R_4$ represents hydrogen, cyano, F, Cl, $C_1$–$C_4$-alkyl, $C_1$–$C_4$-oxyalkyl or carboxy-$C_1$–$C_4$-alkyl, $R_5$ is defined as in claim 1.

6. A pharmaceutical composition containing as an active ingredient an antihypertensively, diuretically or uricosurically effective amount of a compound according to claim 1 in admixture with an inert pharmaceutical carrier.

7. A pharmaceutical composition of claim 6 in the form of a sterile or physiologically isotonic aqueous solution.

8. A composition according to claim 6 or 7 containing from 0.5 to 95% by weight of the said active ingredient.

9. A medicament in dosage unit form comprising an antihypertensively diuretically or uricosutically effective amount of a compound according to claim 1.

10. A medicament of claim 9 in the form of tablets, pills, dragees, capsules, ampoules, or suppositories.

11. A method of combating oedematous, hypertonic and renal insufficiency conditions and of eliminating toxic substances in warm-blooded animals which comprises administering to the said animals an alkylmercapto active compound according to claim 1 either alone or in admixture with an inert pharmaceutical carrier or in the form of a medicament.

12. A method according to claim 11 in which the active compound is administered parenterally in an amount of 0.05 to 100 mg per kg body weight per day.

13. A method according to claim 11 in which the active compound is administered orally in an amount of 0.1 to 500 mg per kg body weight per day.

14. A compound according to claim 1 or a salt thereof, said compound being N-[β-(2-methyl-7-phenyl-imidazo [2,1-b]-1,3,4-thiadiazol-5-yl)-propenoyl]-2-ethyl-piperidine.

15. A compound of claim 1 having the formula

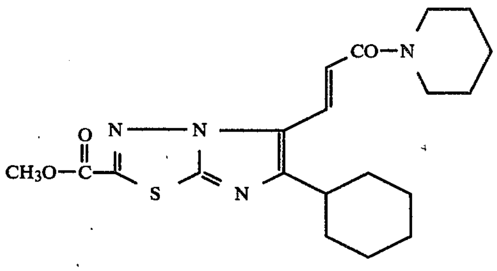

* * * * *

UNITED STATES PATENT AND TRADEMARK OFFICE
CERTIFICATE OF CORRECTION

PATENT NO. : 4,444,770

DATED : April 24, 1984

INVENTOR(S) : Horst Meyer et al

It is certified that error appears in the above-identified patent and that said Letters Patent is hereby corrected as shown below:

| | |
|---|---|
| 1st page, Title and Col. 1, line 2 | Second line, before "Intermediate" insert --New-- |
| Col. 7, line 33 | Delete "atoma" and substitute --atom-- |
| Col. 11, line 31 | Insert a space between "conditions" and "and" |
| Col. 12, line 38 | Delete "for" and substitute --For-- |
| Col. 63, line 40 | Delete end of formula and substitute -- 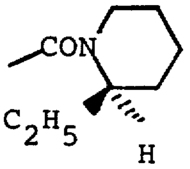 -- |
| Col. 66, line 46 | Delete "substitued" and substitute --substituted-- |
| Col. 69, line 5 | After "1,2" delete "and" and substitute --or-- |

UNITED STATES PATENT AND TRADEMARK OFFICE

CERTIFICATE OF CORRECTION

PATENT NO. : 4,444,770

DATED : April 24, 1984

INVENTOR(S) : Horst Meyer et al

It is certified that error appears in the above-identified patent and that said Letters Patent is hereby corrected as shown below:

Col. 9, line 30 Delete " 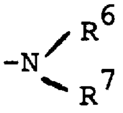 "

and substitute

-- 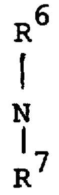 --

Signed and Sealed this

*Thirtieth* Day of *October 1984*

[SEAL]

*Attest:*

GERALD J. MOSSINGHOFF

*Attesting Officer* *Commissioner of Patents and Trademarks*

UNITED STATES PATENT AND TRADEMARK OFFICE
CERTIFICATE OF CORRECTION

PATENT NO. : 4,444,770

DATED : Aaril 24, 1984

INVENTOR(S) :

It is certified that error appears in the above-identified patent and that said Letters Patent is hereby corrected as shown below:

Cols. 25 to 64, line 2 of each — Delete structural formula and substitute

-- 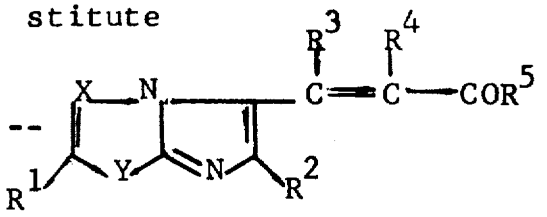 --

Signed and Sealed this

*Tenth* Day of *December 1985*

[SEAL]

*Attest:*

DONALD J. QUIGG

*Attesting Officer* — *Commissioner of Patents and Trademarks*